US012653436B2

(12) United States Patent
Ortega et al.

(10) Patent No.: US 12,653,436 B2
(45) Date of Patent: Jun. 16, 2026

(54) PHYSIOLOGICAL SENSING AND MONITORING SYSTEMS AND METHODS OF IMPLEMENTING THE SAME

(71) Applicant: MDDRIVEN LLC, Clayton, MO (US)

(72) Inventors: Wilman Ortega, Clayton, MO (US); Angela Boone, Clayton, MO (US); Jennifer Fleites, Clayton, MO (US); Carter Fenton, Jr., Clayton, MO (US)

(73) Assignee: MDDRIVEN LLC, Clayton, MO (US)

( * ) Notice: Subject to any disclaimer, the term of this patent is extended or adjusted under 35 U.S.C. 154(b) by 355 days.

(21) Appl. No.: 18/234,589

(22) Filed: Aug. 16, 2023

(65) Prior Publication Data

US 2023/0389848 A1 Dec. 7, 2023

Related U.S. Application Data

(63) Continuation of application No. PCT/US2022/016581, filed on Feb. 16, 2022.

(60) Provisional application No. 63/250,683, filed on Sep. 30, 2021, provisional application No. 63/149,859, filed on Feb. 16, 2021.

(51) Int. Cl.
*A61B 5/00* (2006.01)
*A61B 5/33* (2021.01)

(52) U.S. Cl.
CPC .............. *A61B 5/33* (2021.01); *A61B 5/0006* (2013.01); *A61B 5/6891* (2013.01)

(58) Field of Classification Search
CPC ....... A61B 5/33; A61B 5/0006; A61B 5/6891; A61B 5/4836; A61B 2560/0443; A61B 5/6805; A61B 5/6887; A61B 7/003; A61B 7/04
See application file for complete search history.

(56) References Cited

U.S. PATENT DOCUMENTS 6,416,471 B1 * 7/2002 Kumar ................. A61B 5/0022
128/903
10,424,183 B1 9/2019 Kahn
(Continued)

FOREIGN PATENT DOCUMENTS

CN 104887004 5/2015
KR 101863005 5/2018
WO WO2022177978 8/2022

*Primary Examiner* — Scott M. Getzow
(74) *Attorney, Agent, or Firm* — Blynn L. Shideler; Krisanne Shideler; BLK Law Group

(57) ABSTRACT

A method of monitoring physiological parameters of a user comprises providing a system for monitoring physiological parameters having a pliable body, with a plurality of physiologic sensing devices mounted within the pliable body, the plurality of physiologic sensing devices including sensors detecting at least lung sounds, heart sounds and EKG signals, and a wireless communication device for transmitting at least lung sounds, heart sounds and EKG signals detected; Removably positioning the system on the backrest of a chair; Poisoning the system against the back of the user; Sensing at least lung sounds, heart sounds and EKG signals from a subject from the posterior chest of the user via the system; and Transmitting at least lung sounds, heart sounds and EKG signals detected through the posterior chest of the user to a computer to monitor physiological parameters of the user.

18 Claims, 13 Drawing Sheets

(56) References Cited

U.S. PATENT DOCUMENTS

| | | | |
|---|---|---|---|
| 2005/0078533 A1* | 4/2005 | Vyshedskiy | A61B 5/0006 |
| | | | 365/200 |
| 2007/0270665 A1* | 11/2007 | Yang | G16H 40/67 |
| | | | 600/595 |
| 2012/0253216 A1* | 10/2012 | Fu | A61B 7/04 |
| | | | 600/529 |
| 2013/0310657 A1 | 11/2013 | Sullivan | |
| 2016/0089059 A1 | 3/2016 | Hu | |
| 2020/0060641 A1* | 2/2020 | Shekhar | A61B 5/14542 |

* cited by examiner

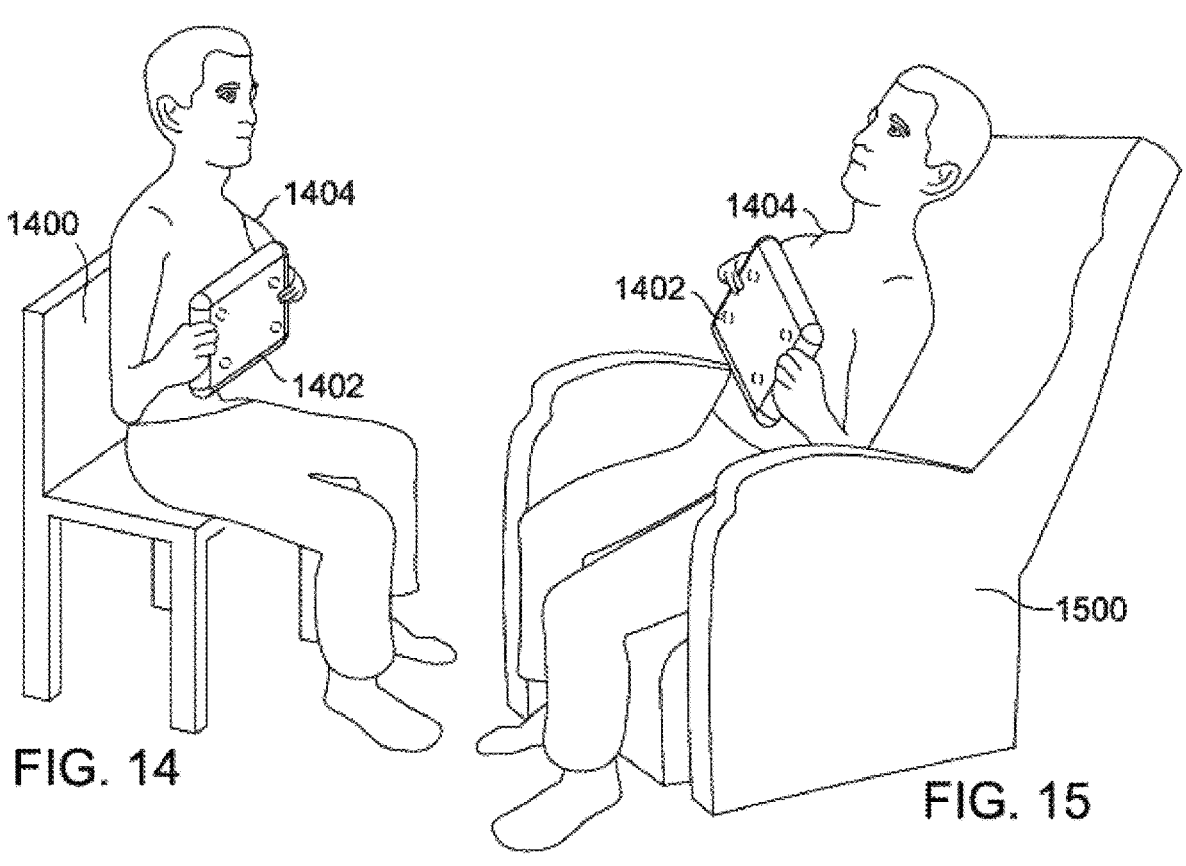
FIG. 14
FIG. 15
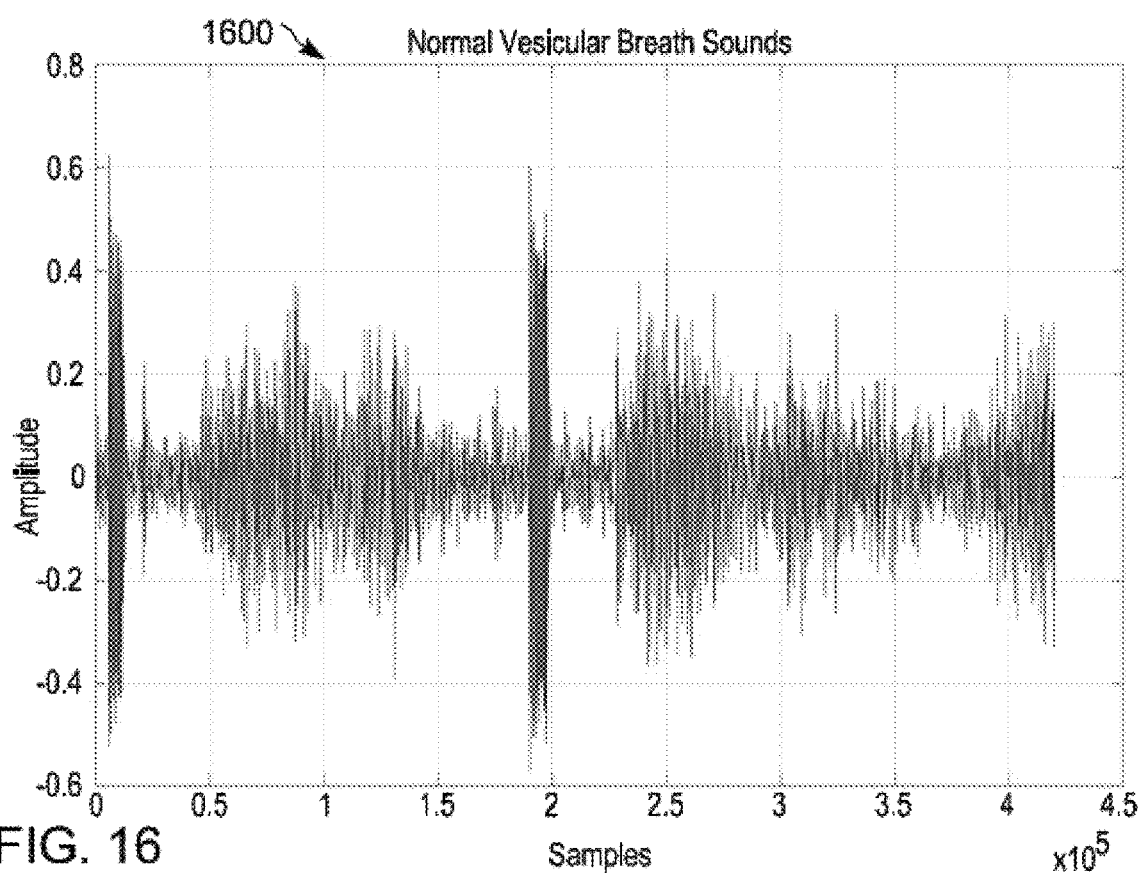
FIG. 16

1700

Normal Contour

1800

High-Pitched Wheezing

PHYSIOLOGICAL SENSING AND MONITORING SYSTEMS AND METHODS OF IMPLEMENTING THE SAME

RELATED APPLICATIONS

The present application is a continuation of International Patent Application PCT/US2022/016581 filed Feb. 16, 2022 and published as publication number WO 2022/177,978 on Aug. 25, 2022. International Patent Application PCT/US2022/016581 claims the benefit of U.S. Provisional Application No. 63/149,859 filed Feb. 16, 2021 and U.S. Provisional Application No. 63/250,683 filed Sep. 30, 2021. The entire disclosures of the above applications and publication are incorporated herein by reference.

FIELD OF THE INVENTION

The present invention relates to physiological sensing and monitoring systems and methods of implementing or using the same.

BACKGROUND OF THE INVENTION

This section provides background information related to the present disclosure which is not necessarily prior art.

Monitoring devices commonly include one or more sensors for collecting physiological information of individuals. Each device may be strategically positioned at a particular portion of an individual to collect such physiological information. For example, some devices such as pillows may contact an individual's neck and head region, and other devices such as car seats may contact an individual's back while the individual is driving.

In the written opinion of International Patent Application PCT/US2022/016581, U.S. Patent Application 2016-0089059 is disclosed as relevant to the present invention. This application, owned by Darma, Inc. discloses physiological sensing and monitoring systems including a system implementing a cushion upon which the user can sit.

In the written opinion of International Patent Application PCT/US2022/016581, U.S. Patent Application 2013-0310657 is disclosed as relevant to the present invention. U.S. Patent Application 2013-0310657, owned by Sono-medical Pty Ltd, discloses a physiological sensing and monitoring systems including a system implementing sensors within a mat defining a sensing are for the patient.

In the written opinion of International Patent Application PCT/US2022/016581, U.S. Pat. No. 10,424,183 is disclosed as relevant to the present invention. U.S. Pat. No. 10,424,183, owned by DP Technologies, Inc, discloses a physiological sensing and monitoring systems formed as a "smart seat", such as a car seat or office chair, having physiologic sensors mounted in the seating surfaces.

In the written opinion of International Patent Application PCT/US2022/016581, Chinese Patent publication 104887004 is disclosed as relevant to the present invention. Chinese Patent publication 104887004, owned by SHEN-SHEN MIANCHONG TECHNOLOGY CO, LTD, discloses a physiological sensing and monitoring systems formed as an "intelligent pillow" monitoring human physiological parameters, and comprises a pillow body with accelerometers and photoelectric sensor and associated circuitry.

In the written opinion of International Patent Application PCT/US2022/016581, Korean Patent publication 101863005 is disclosed as relevant to the present invention. Korean Patent publication 101863005 discloses a physiological sensing and monitoring systems formed as a seat cushion with physiologic monitoring sensors therein.

The above cited patents and published application give a detailed overview of the state of the art relating to the present invention.

SUMMARY OF THE INVENTION

This section provides a general summary of the disclosure, and is not a comprehensive disclosure of its full scope or all of its features.

According to one aspect of the present disclosure, a method of monitoring physiological parameters of a user includes positioning a pliable object against a chest of the user. The pliable object includes one or more physiological sensing devices. The method further includes sensing at least one physiological parameter of the user with the one or more physiological sensing devices when the one or more physiological sensing devices are adjacent to the chest of the user, and communicating the at least one physiological parameter of the user to a computing device to allow for monitoring of the physiological parameter.

One aspect of the present invention provides a system for monitoring physiological parameters of a user, the system including a pliable body configured to be removably positioned on the backrest of a chair; a plurality of physiologic sensing devices mounted within the pliable body, the plurality of physiologic sensing devices including sensors configured for detecting at least lung sounds, heart sounds and EKG signals from the posterior chest wall of a subject; a wireless communication device for transmitting at least lung sounds, heart sounds and EKG signals detected from the posterior chest wall of the subject; and a computer configured to receive and display at least the transmitted lung sounds, heart sounds and EKG signals detected through the posterior chest of the user to monitor physiological parameters of the user.

One aspect of the present invention provides a method of monitoring physiological parameters of a user, the method comprising the steps of: Providing a system for monitoring physiological parameters of a user having a pliable body, with a plurality of physiologic sensing devices mounted within the pliable body, the plurality of physiologic sensing devices including sensors detecting at least lung sounds, heart sounds and EKG signals from a subject, and a wireless communication device for transmitting at least lung sounds, heart sounds and EKG signals detected from the subject; Removably positioning the system for monitoring physiological parameters of the user on the backrest of a chair; Poisoning the system for monitoring physiological parameters of the user against the back of the user by having the user sit in the chair; Sensing at least lung sounds, heart sounds and EKG signals from a subject from the posterior chest of the user via the system for monitoring physiological parameters of the user; and Transmitting at least lung sounds, heart sounds and EKG signals detected through the posterior chest of the user to a computer to monitor physiological parameters of the user.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

These and other advantages of the present invention will be clarified in connection with the following detailed description of the invention taken in connection with the associated figures.

BRIEF DESCRIPTION OF THE DRAWINGS

The drawings described herein are for illustrative purposes only of selected embodiments and not all possible implementations, and are not intended to limit the scope of the present disclosure.

FIG. 14 is an isometric view of a chair, a user sitting in the chair, and a pliable object positioned against the user's chest according to another example embodiment of the present disclosure.

FIG. 15 is an isometric view of a reclining chair, a user reclining in the chair, and a pliable object positioned against the user's chest according to this embodiment of the present disclosure.

FIG. 16 is a graph of a signal representing normal vesicular lung sounds from a user.

Corresponding reference numerals indicate corresponding parts and/or features throughout the several views of the drawings.

DETAILED DESCRIPTION OF THE INVENTION

Figure 1:
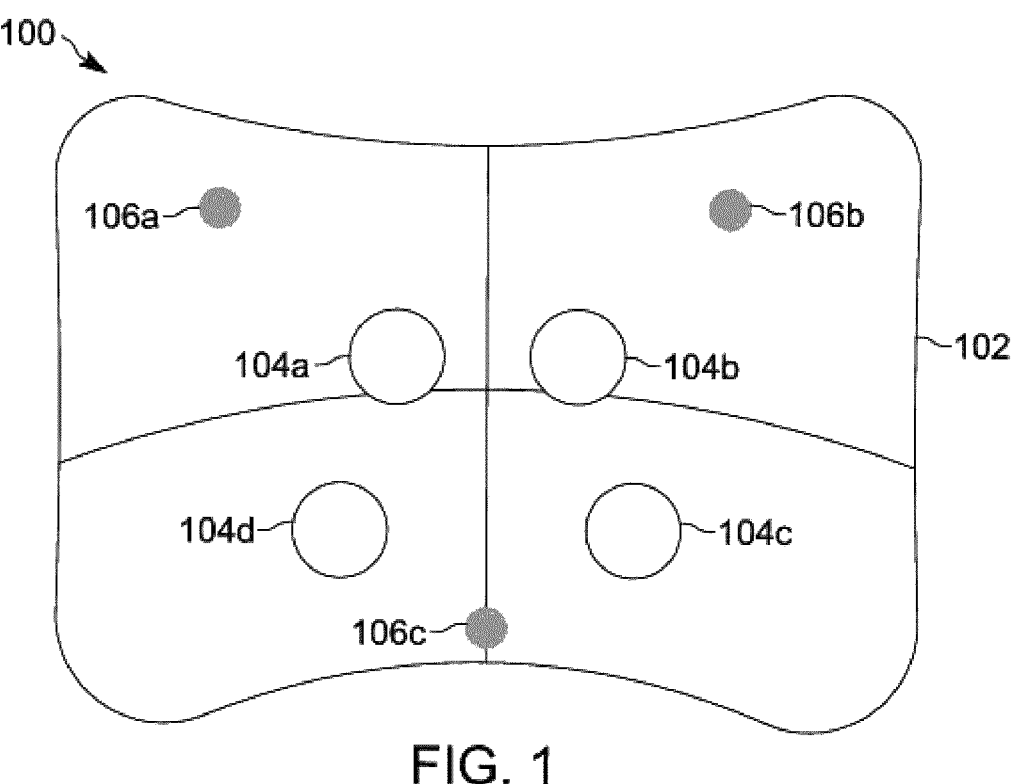
FIG. 1 is a front elevation view of a pillow including stethoscope heads and electrocardiogram leads for obtaining one or more vital signs according to one example embodiment of the present disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments will now be described more fully with reference to the accompanying drawings.

Systems and methods for sensing and monitoring physiological parameters of a user are explained herein. In some embodiments, the systems and methods may include positioning a pliable object such as a pillow, a mat, a pad, etc. against a chest (or a back) of a user. In such examples, the pliable object includes one or more physiological sensing devices. The systems and methods further include sensing at least one physiological parameter of the user with the one or more physiological sensing devices when the one or more physiological sensing devices are adjacent to the chest (or the back) of the user, and communicating the at least one physiological parameter of the user to a computing device to allow for monitoring of the physiological parameter. The physiological parameter(s) may include, for example, a heart rate, electrical activity in the heart, blood pressure, cardiac output, cardiac ejection fraction, body temperature, sounds associated with a heart, lungs, etc., blood circulation characteristics, pulse rate, oxygen saturation, etc.

A user may be in different positions when employing any one of the pliable objects disclosed herein. For example, the user may be sitting in a chair in an upright position, a reclined position, etc. In such examples, the pliable object may be positioned between a chair back and the user's chest/back, held against the user's chest while the user sits in the chair, etc. In other examples, the user may be lying down on a floor, a bed, etc. in a supine position or a prone position. In such examples, the pliable object may be positioned between the user's back/chest and the floor/bed, held against the user's chest while the user is lying down, etc. In further examples, the user may be standing up. In such examples, the pliable object may be positioned between the user's back or chest and a wall, held against the user's chest, etc.

The methods disclosed herein may be implemented with various different systems. For example, a system for sensing and monitoring physiological parameters of a user according to one example embodiment of the present disclosure is illustrated in FIG. 1, and indicated generally by reference number 100. As shown in FIG. 1, the system 100 includes a body 102, and one or more sensing devices positioned to sense one or more physiological parameters of a user when the user is in contact with the body 102. The system 100 further includes a control circuit (not shown) in communication with the sensing devices for receiving data related to the physiological parameters of the user.

The body 102 may be any suitable device for contacting a user. For example, the body 102 may have a shape that substantially corresponds to a portion of the user's body such as the user's back, chest, etc. In some examples, the body 102 may be at least somewhat compressible allowing the shape of the body 102 to change and conform to the user's body. In the particular example of FIG. 1, the body 102 is a pillow. In other examples, the body 102 may be another suitable pliable object such as a mat, a pad, etc. as further explained herein.

As shown in FIG. 1, the sensing devices include four stethoscope heads 104a, 104b, 104c, 104d, and three electrocardiogram (EKG or ECG) leads 106a, 106b, 106c. In such examples, the stethoscope heads 104a, 104b, 104c, 104d may be wired with microphones or other suitable transducers for capturing data corresponding to upper and lower portions of each lung of the user. Such data may be in the form of analog waveforms representing sounds associated with the user's lung(s). The EKG (or ECG) leads 106a, 106b, 106c capture data corresponding to cardiac electrical potential waveforms (e.g., produced when the contraction of a heart of the user is contracted).

In other examples, more or less stethoscope heads and/or EKG leads may be employed if desired. For example, the system 100 may include a single stethoscope head, two stethoscope heads, five stethoscope heads, etc. Additionally, the system 100 may include any suitable number of EKG leads including, for example, between one EKG lead to nine EKG leads. For example, the system 100 may include a single EKG lead, four EKG leads, six EKG leads (e.g., precordial leads V1-6), etc.

In other examples, the system 100 of FIG. 1 may include one or more additional and/or alternative devices for sensing vital signs and/or other desirable data. For example, the system 100 may include one or more temperature probes, pulse oximeters, blood pressure cuffs, photoplethysmograph (PPG) sensors, ballistocardiograph (BCG) sensors, ultrasound probes, etc. In various embodiments, the body (e.g., the pillow) 102 may include one or more ports (e.g., USB ports, etc.) along its side surface, rear surface, etc. The ports may be in communication with the control circuit.

Sensing devices such as temperature probes, pulse oximeters, blood pressure cuffs, scales (e.g., digital scales), ultrasound probes, chest/abdominal belts, nasal probes with microphones, flow/pressure sensors, etc. may be detachably coupled to the ports. In other examples, the additional and/or alternative sensing devices may be physically attached to a portion of the body 102 and/or in communication with the control circuit as further explained below.

In various embodiments, the chest/abdominal belts, the nasal probes with microphones, and/or the flow/pressure sensors may be employed to assist in a home sleep study. For example, the chest/abdominal belts, the nasal probes with microphones, and/or the flow/pressure sensors may be positioned on the user to check for abdominal and chest effort, snoring, airflow, etc. In such examples, the user may be in a reclined position, a supine position sleeping, etc. as further explained herein.

Figure 2:
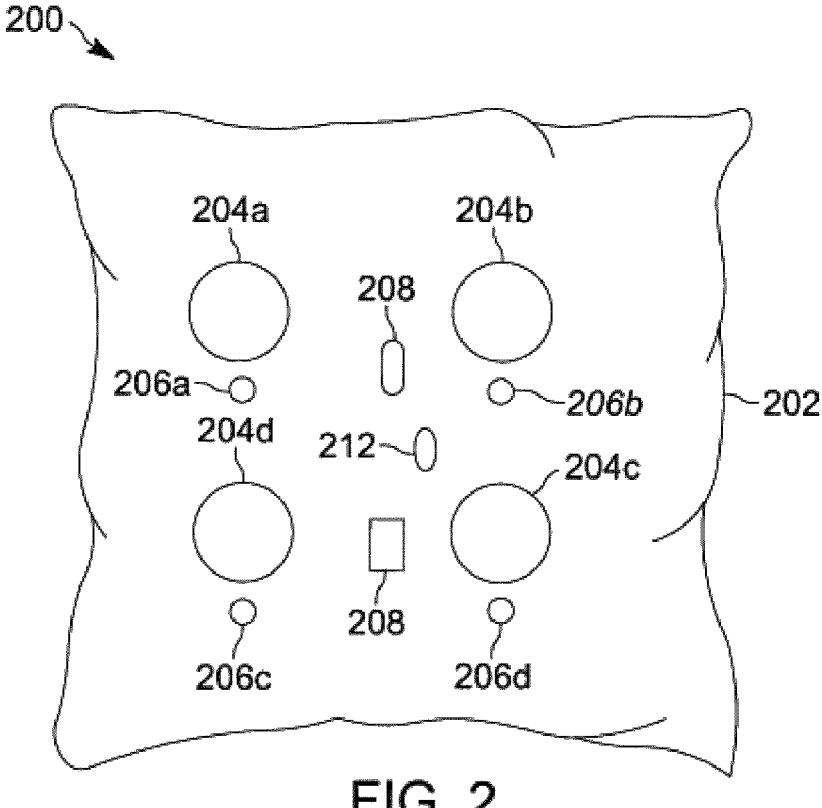
FIG. 2 is a front elevation view of a pillow including a photoplethysmograph (PPG) sensor and a ballistocardiograph (BCG) sensor according to another example embodiment of the present disclosure.

FIG. 2 illustrates a system 200 including a body 202 and sensing devices positioned to sense one or more physiological parameters of a user when the user is in contact with the body 202. The system 200 further includes a control circuit (not shown) in communication with the sensing devices. In such examples, the control circuit receives data related to the vital signs of the user.

In the example of FIG. 2, the body 202 is a pillow having a shape that substantially corresponds to a portion of the user's body such as the user's back, chest, etc. The pillow may be at least somewhat compressible to conform to the user's body. In other examples, the body 202 may be another suitable pliable object such as a mat, a pad, etc.

The sensing devices of FIG. 2 may include various devices for sensing different vital signs of the user. For example, the sensing devices of FIG. 2 include four stethoscope heads 204a, 204b, 204c, 204d, four EKG leads 206a, 206b, 206c, 206d, a PPG sensor 208, a BCG sensor 210, and a temperature sensor 212. The stethoscope heads 204a, 204b, 204c, 204d and the EKG leads 206a, 206b, 206c, 206d of FIG. 2 may function in a similar manner as the stethoscope heads 104a, 104b, 104c, 104d and the EKG leads 106a, 106b, 106c of FIG. 1. The temperature sensor 212 captures data corresponding to a body temperature of the user.

The PPG sensor 208 of FIG. 2 captures data corresponding to a heart rate of the user. For example, the PPG sensor 208 may include an LED or another suitable light source for emitting an infrared light that penetrates the skin and blood vessels, and a photodetector for detecting the intensity of reflected light. In such examples, the PPG sensor 208 may detect a change in blood volume circulating in the user. In some examples, the PPG sensor 208 may be used to measure a pulse rate, measure oximetry (e.g., oxygen (O2) saturation), a glucose level, and/or detect and monitor systemic blood pressure (e.g., aided by data from one or more of the posterior chest EKG leads 206a, 206b, 206c, 206d) as further explained herein. In various embodiments, the PPG sensor 208 may be used for calibration purposes if desired.

In the example of FIG. 2, the PPG sensor 208 may be embedded in the pillow and employ a posterior chest approach concept. In other embodiments, the system 200 may include another PPG sensor (in addition to or instead of the sensor 208). This PPG sensor may be a finger probe connected to the control circuit via a wired USB cable or via wireless communication (e.g., Bluetooth, WiFi, etc.).

The BCG sensor 210 of FIG. 2 captures data corresponding to ballistic forces of the heart caused by the sudden ejection of blood into blood vessels with each heartbeat, breath, and/or body movement. The BCG sensor 210 may include, for example, an accelerometer to capture vibrations generated by the movement of blood in the user. In some examples, the BCG sensor 210 may be used for detecting and monitoring a blood pressure, a respiratory rate, a pulse rate, a cardiac ejection fraction and/or a cardiac output. For example, a cardiac ejection fraction and/or a blood pressure of a user may be obtained based on data from the PPG sensor 208 and data from the EKG leads 206a, 206b, 206c, 206d, as further explained herein.

Figures 3, 4:
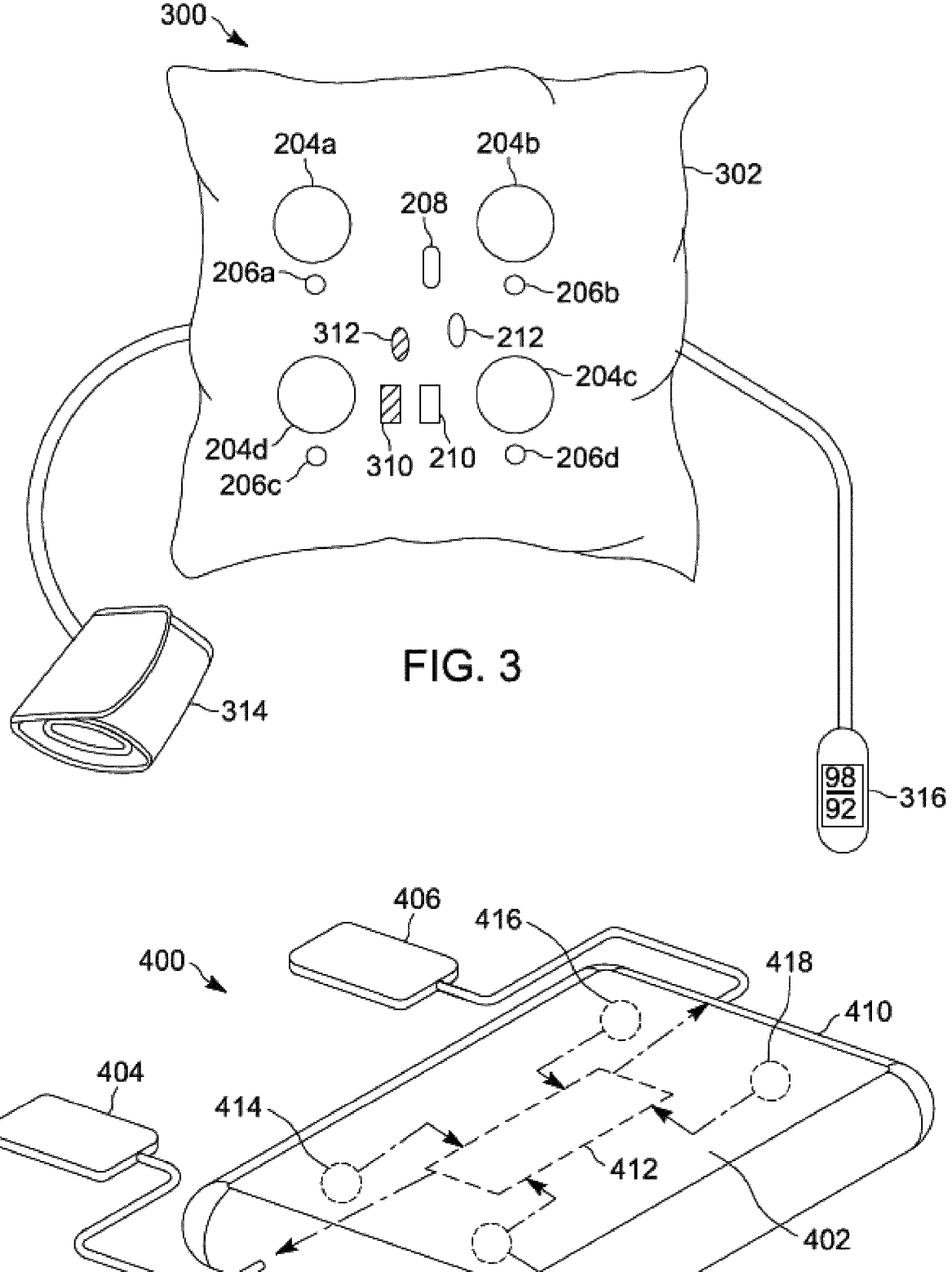
FIG. 3 is a front view of a pillow including a sphygmomanometer and a pulse oximeter according to another example embodiment of the present disclosure.
FIG. 4 is a perspective view of a pliable object including defibrillator paddles according to another example embodiment of the present disclosure.

FIG. 3 illustrates a system 300 including a body 302 and sensing devices for sensing one or more physiological parameters (e.g., vital signs) of a user when the user is in contact with the body 302. The sensing devices of FIG. 3 are in communication with a control circuit (not shown), as explained herein.

The system 300 is substantially similar to the system 200 of FIG. 2, but includes additional sensing devices. For example, the body 302 is a pillow (e.g., a compressible pillow) similar to the body 202 of FIG. 2. The sensing devices of FIG. 3 include the stethoscope heads 204a, 204b, 204c, 204d, the EKG leads 206a, 206b, 206c, 206d, the PPG sensor 208, the BCG sensor 210, and the temperature sensor 212 of FIG. 2. The sensing devices of FIG. 3 further include an additional BCG sensor 310, an additional temperature sensor 312, a sphygmomanometer 314, and a pulse oximeter 316. The BCG sensor 310 and the temperature sensor 312 function in a similar manner as the BCG sensor 210 and the temperature sensor 212 of FIG. 2.

In the example of FIG. 3, the sphygmomanometer 314 is used to measure a blood pressure of the user. For example, and as shown in FIG. 3, the sphygmomanometer 314 includes an inflatable cuff (e.g., an inflatable rubber cuff) for wrapping around an arm of the user. The sphygmomanometer 314 may be controlled (e.g., activated, deactivated, etc.) by the control circuit and/or manually controlled to inflate and deflate the cuff.

The pulse oximeter 316 may be used to obtain an oxygen saturation level, a pulse rate, a glucose level, and/or a blood pressure. As shown in FIG. 3, the pulse oximeter 316 includes a display for showing the oxygen saturation level and a pulse rate. In the example of FIG. 3, the oxygen saturation level is shown as 98%, and the pulse rate is shown as 92 beats per minute.

In various embodiments, the sphygmomanometer 314 and/or the pulse oximeter 316 may be used for calibration purposes if desired.

In the example of FIG. 3, the sphygmomanometer 314 and the pulse oximeter 316 are coupled to the body 302. For example, the body 302 may include one or more ports (e.g., USB ports, etc.) in communication with the control circuit. Each port may be positioned along a side surface, a rear surface, etc. of the body 302. In such examples, the sphygmomanometer 314 and the pulse oximeter 316 may be detachably coupled to the ports. In other examples, the sphygmomanometer 314 and/or the pulse oximeter 316 may be physically attached to a portion of the body 102 and/or in communication with the control circuit as further explained below.

The sphygmomanometer 314 and the pulse oximeter 316 may be in communication with the control circuit. In such examples, the control circuit may receive signals from the sphygmomanometer 314 and/or the pulse oximeter 316. Additionally, the sphygmomanometer 314 and/or the pulse oximeter 316 may be controlled (e.g., activated, inflated, etc.) by signals received from the control circuit and/or other sources such as user-activated switches (e.g., ON/OFF buttons on the sphygmomanometer 314 and the pulse oximeter 316).

In other examples, the systems herein may include one or more devices that activate, perform a function, etc. based on received instructions, sensed physiological parameters, etc. For example, FIG. 4 illustrates a system 400 including a body 402 and two defibrillator paddles 404, 406 extending from opposing sides 408, 410 of the body 402. As shown, the system 400 further includes a control circuit (e.g., a microcontroller, etc.) 412 in communication with the defibrillator paddles 404, 406, and sensing devices 414, 416, 418, 420 in communication with the control circuit 412. In the example of FIG. 4, the body 402 is a pliable object such as a pillow, a mat, a pad, etc. Additionally, any one of the sensing devices 414, 416, 418, 420 may be an EKG lead, a stethoscope head, and/or another suitable sensor such as the sensors disclosed herein.

In the example of FIG. 4, the defibrillator paddles 404, 406 may be coupled to the body 402 through ports positioned on the sides 408, 410 of the body 402. The ports are in communication with the control circuit 412. In such examples, the defibrillator paddles 404, 406 may be detachably coupled to the ports. Additionally, the defibrillator paddles 404, 406 of FIG. 4 may be movable. For example, when not being used, the defibrillator paddles 404, 406 may be moved and stored in one or more compartments on a backside of the body 402. If needed, the paddles 404, 406 may be moved (e.g., removed from the compartment(s)) and positioned against the user's chest.

The defibrillator paddles 404, 406 may generate an electric shock based on sensed data from one or more of the sensing devices 414, 416, 418, 420. For example, the defibrillator paddles 404, 406 may be controlled to shock the user in response to sensed physiological parameters of the user. For instance, the control circuit 412 may analyze sensed physiological parameters of the user to determine a cardiac rhythm (e.g., using a rhythm analyzing algorithm) and whether a shock needs to be delivered based on the cardiac rhythm. In such examples, the control circuit 412 may generate a signal to instruct the paddles 404, 406 to shock the user when the paddles 404, 406 are positioned against the user's chest. In other examples, EKG and/or the control circuit 412 incorporated into the body 402 may analyze the cardiac rhythm. In such examples, commands to deliver a shock may be provided from a computing device (e.g., a smart phone, a tablet, etc.) in communication with the control circuit 412 based on the cardiac rhythm.

In some embodiments, the system 400 of FIG. 4 may include a control unit (not shown) to operate the defibrillator paddles 404, 406. For example, the control unit may include various inputs for controlling the paddles 404, 406. For instance, the control unit may include one or more power inputs (e.g., user-activated buttons) to activate and/or deactivate the paddles 404, 406. Such inputs may, for example, control a switch to connect and/or disconnect the paddles 404, 406 to a power source. Additionally, the control unit may include a defibrillate input (e.g., a user-activated button) that controls when the paddles 404, 406 provide a shock.

Figures 5, 6:
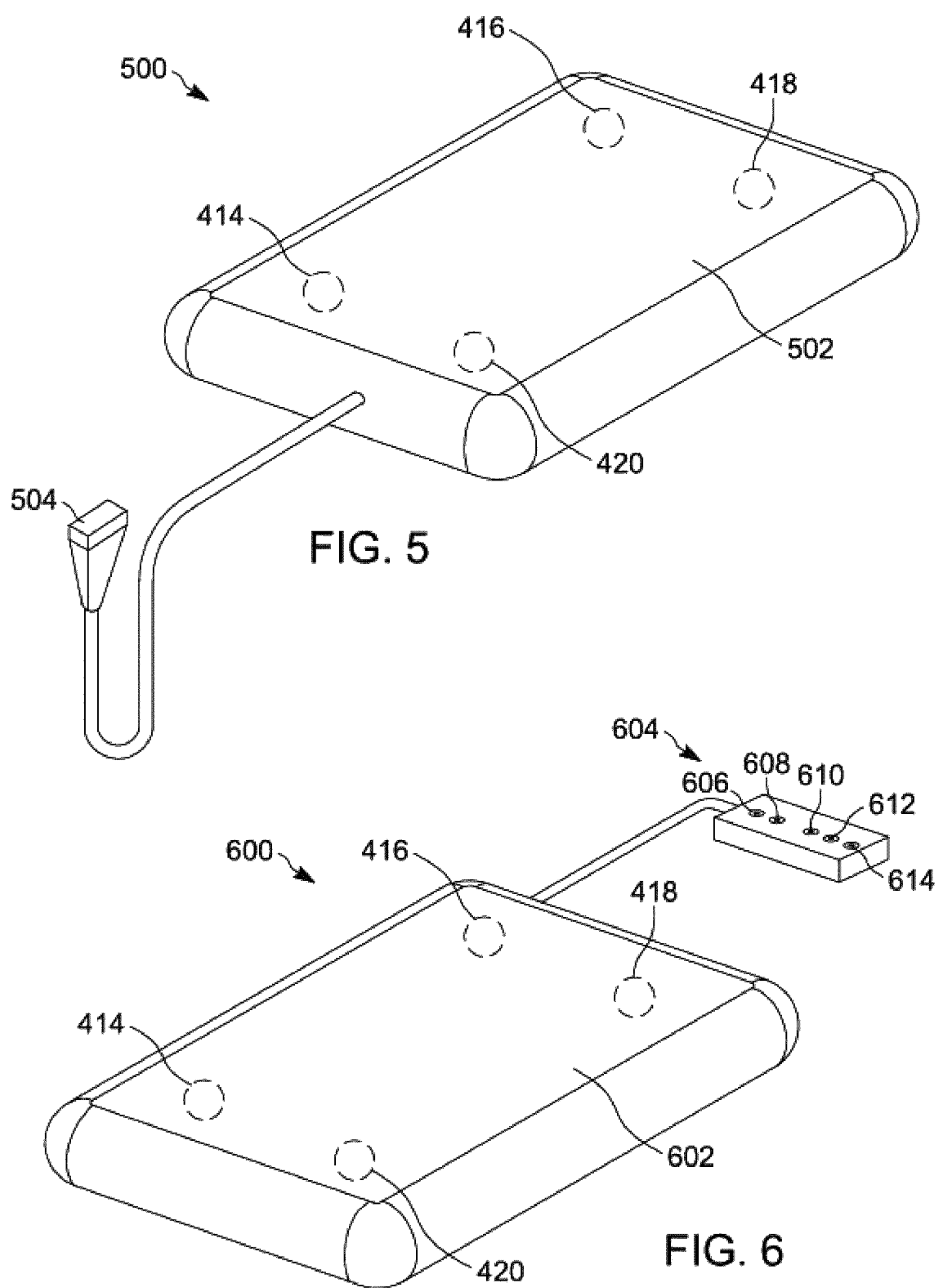
FIG. 5 is a perspective view of a pliable object including an ultrasound probe according to another example embodiment of the present disclosure.
FIG. 6 is a perspective view of a pliable object including a user control device according to another example embodiment of the present disclosure.

FIG. 5 illustrates another example system 500 including a body 502, the sensing devices 414, 416, 418, 420 of FIG. 4, and an ultrasound probe 504 extending from a side of the body 502. The ultrasound probe 504 may employ different modes (e.g., an A-mode, a B-mode, a M-mode and a Doppler mode) as is conventional in the medical field. Although not shown, the system 500 further includes a control circuit (e.g., similar to the control circuit 412 of FIG. 4) that is in communication with the sensing devices 414, 416, 418, 420 and the ultrasound probe 504. In the example of FIG. 5, the body 502 is a pliable object such as a pillow, a mat, a pad, etc.

In the example of FIG. 5, the ultrasound probe 504 may include various components that produce sound waves that bounce off body tissues of the user and receive echoes based on the produced sound waves. For example, the ultrasound probe 504 may include a transmitter pulse generator for generating sound waves, a transducer for receiving echoes, one or more compensating amplifiers, a user control unit, a processor (e.g., a digital processor), etc. The ultrasound probe 504 may be utilized for lung, cardiac, and/or vessel evaluations for conditions such as but not limited to evaluation of cardiac function (ejection fraction, contractility, etc.), valvular structures, heart muscle, pericardium and pericardial effusions, and pulmonary evaluations such as pleural effusions, pneumothorax, normal lung evaluations, pulmonary edema, etc.

The ultrasound probe 504 may be coupled to the body 502 through a port on the body 502. This port may be in communication with the control circuit for providing one or more signals (e.g., representing echoes) from the probe 504 to the control circuit. In such examples, the ultrasound probe 504 may be detachably coupled to the body 502 (via the port).

Additionally the ultrasound probe 504 may be movable about the user's body as necessary. When used, the user or another individual may apply gel on the user's chest or the probe 504 as is conventional. The ultrasound probe 504 may be moved and stored in a compartment on a backside of the body 502 when the probe 504 is not being used.

Further, in the example of FIG. 5, the system 500 includes one ultrasound probe 504. However, it should be apparent that the system 500 (and/or any other system disclosed herein) may include any suitable number of ultrasound probes. For example, the system 500 may include two ultrasound probes, three ultrasound probes, four ultrasound probes, etc. in communication with the control circuit.

FIG. 6 illustrates another example system 600 including a body 602, the sensing devices 414, 416, 418, 420 of FIG. 4, and a user control device (e.g., a handheld controller, etc.) 604 extending from a side of the body 602. The user control device 604 may be coupled (e.g., detachably coupled) to the body 602 through a port on the body 602. This port may be in communication with a control circuit (not shown) to provide one or more signals from the device 604 to the control circuit. In the example of FIG. 6, the body 602 is a pliable object such as a pillow, a mat, a pad, etc.

As shown in FIG. 6, the user control device 604 includes multiple selectable inputs for controlling features of the system 600, conveying messages, etc. In the example of FIG. 6, the device 604 includes five selectable inputs 606, 608, 610, 612, 614. In other examples, the device 604 may include more or less inputs if desired.

The selectable inputs 606, 608, 610, 612, 614 of the user control device 604 may provide different functions. For example, the input 606 may turn on components (e.g., the sensing devices 414, 416, 418, 420, the control circuit, etc.) in the body 602, and the input 608 may turn off components in the body 602. In such examples, the user (or another individual) may select (e.g., push) the input 606 to provide power to the components and/or select the input 608 to interrupt power to the components. In other examples, the inputs 606, 608 may be combined into one input. In such examples, the user (or another individual) may select (e.g., push) the input a first time to provide power to the components and/or select the input a second time to interrupt power to the components.

Additionally the selectable inputs 610, 612, 614 of the user control device 604 may function to communicate one or more messages to a computing device. In such examples, the user control device 604 may provide one or more signals representing a particular message to the control circuit based on the selected input. The control circuit may communicate with the computing device (e.g., a cloud-based server) to notify proper medical personnel. This communication may be provided wirelessly through Bluetooth, WiFi, cellular, etc. protocols. In other examples, the user control device 604 may communicate with the computing device if desired.

For example, the input 610 may convey a message signifying the user is okay, the input 612 may convey a message signifying a need for help with certain medical needs identified (e.g., based on the devices 414, 416, 418, 420), and the input 614 may convey a message signifying that a need for immediate help (e.g., an emergency). In some examples, the inputs 610, 612, 614 may include different indicators (e.g., colors, numbers, letters, etc.) representing the different messages to allow the user to identify which input is desirable to select. For example, the input 610 may be green, the input 612 may be yellow, and the input 614 may be red.

Figures 7, 8, 9:
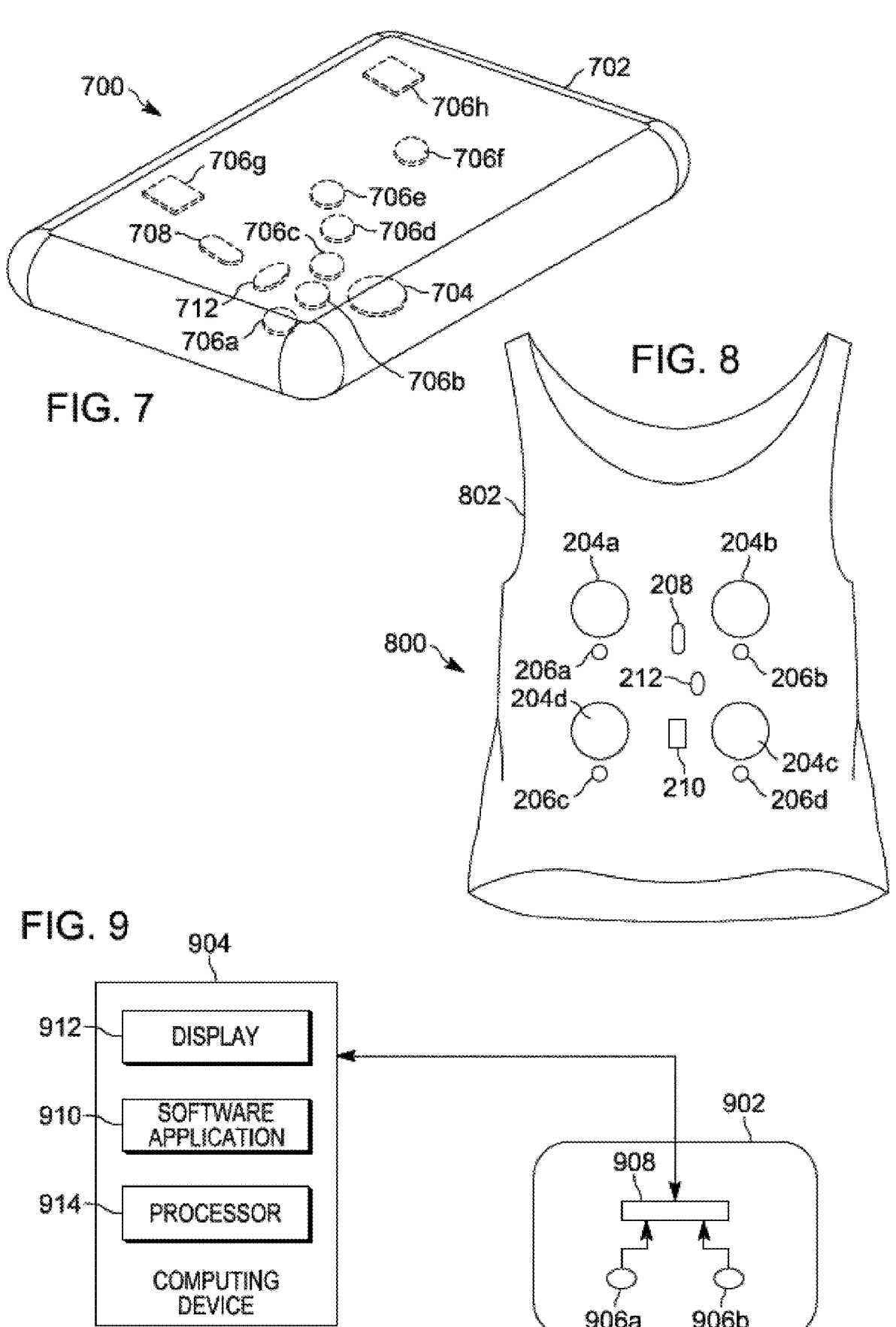
FIG. 7 is a perspective view of a pliable object including six precordial EKG leads according to another example embodiment of the present disclosure.
FIG. 8 is a front elevation view of a vest including a PPG sensor and a BOG according to another example embodiment of the present disclosure.
FIG. 9 is a schematic block diagram of a system including a computing device, and a body such as a pliable object having sensing devices and a control circuit in communication with the computing device according to another example embodiment of the present disclosure.

FIG. 7 illustrates another example system 700 including a body 702, various sensing devices for sensing physiological parameters of a user, and a control circuit (not shown) in communication with the sensing devices. In the example of FIG. 7, the body 702 is a pliable object such as a pillow, a mat, a pad, etc. that may be positioned against the user's chest.

In FIG. 7, the sensing devices include a stethoscope head 704, a PPG sensor 708, a temperature sensor 712, and multiple EKG leads 706a-h. The stethoscope head 704, the PPG sensor 708, the temperature sensor 712, and the EKG leads 706a may function and be used in a similar manner as other stethoscope heads, PPG sensors, temperature sensors, and EKG leads disclosed herein. In the example of FIG. 7, the EKG leads 706a-f may represent, for example, precordial leads V1 through V6, and the EKG leads 706g-h may represent right and left arm EKG leads.

Although the bodies 102, 202, 302, 402, 502, 602, 702 of FIGS. 1-7 are shown as pliable objects (e.g., pillows, mats, pads, etc.), it should be appreciated that any one of the systems may include another suitable body type that may be used to contact a portion of a user's body such as a user's back, chest, etc. For example, any one of the systems disclosed herein may include a body in the form of a vest, a backpack, etc. For instance, FIG. 8 illustrates a system 800 including a body 802, and the stethoscope heads 204a, 204b, 204c, 204d, the EKG leads 206a, 206b, 206c, 206d, the PPG sensor 208, the BCG sensor 210, and the temperature sensor 212 of FIG. 2. In the example of FIG. 8, the body 802 is a vest wearable by a user.

As shown in FIG. 8, the vest includes a front side and a back side. When the vest is worn by a user, the front side is positioned adjacent to the chest of the user (e.g., an anterior portion of the user) and the back side is positioned adjacent to the back of the user (e.g., a posterior portion of the user).

The sensing devices of FIG. 8 may be positioned on a back side and/or a front side of the vest. For example, the stethoscope heads 204a, 204b, 204c, 204d, the EKG leads 206a, 206b, 206c, 206d, the PPG sensor 208, the BCG sensor 210, and the temperature sensor 212 may be positioned on the back side of the vest for collecting one or more physiological parameters (e.g., vital signs) of the user when the user is wearing the vest. As such, when the vest is worn by the user, the stethoscope heads 204a, 204b, 204c, 204d, the EKG leads 206a, 206b, 206c, 206d, the PPG sensor 208, the BCG sensor 210, and the temperature sensor 212 are adjacent to portions of the user's back. In other examples, one or more of the various sensing devices of FIG. 8 may be positioned on the front side of the vest and adjacent to portions of the user's chest. In various embodiments, the vest may be sized and shaped to conform to the user's body such that the sensing devices are in close proximity, and in some cases in contact, with the user's back and/or chest.

In other examples, any one or more of the stethoscope heads 204a, 204b, 204c, 204d, the EKG leads 206a, 206b, 206c, 206d, the PPG sensor 208, the BCG sensor 210, and the temperature sensor 212 may be positioned on the front side of the vest if desired.

In various embodiments, any one of the systems disclosed herein may include a body in the form a backpack-like shape. In such examples, the body may include a panel and one or more straps extending between portions of the panel. One or more sensing devices (e.g., any one or more of the sensing devices disclosed herein) may be positioned on the panel. When the body is worn by the user, the panel may be adjacent to the user's back and the one or more straps may extend around the user's chest and/or shoulders to secure the body to the user. In other examples, the panel may be adjacent to the user's chest and the one or more straps may extend around the user's back when the body is worn by the user. As such, the sensing devices positioned on the panel may be adjacent to portions of the user's back or chest.

Although the systems 100, 200, 300, 400, 500, 600, 700, 800 of FIGS. 1-8 are shown with a specific number of particular sensing devices, it should be apparent that any one of the systems may include another suitable number of sensing devices if desired. For example, the system 100 of FIG. 1 may include a single EKG lead, a single stethoscope head, or four EKG leads and five stethoscope heads. The system 200 of FIG. 2 may include, for example, three EKG leads, two stethoscope heads, two PPG sensors, and two BCG sensors, etc. Additionally, although the sensing devices of FIGS. 1-8 are shown at specific locations relative to their corresponding body, it should be apparent that the sensing devices may be positioned at any suitable location to sense one or more physiological parameters of the user. For example, some of the sensing devices may be embedded within the body (e.g., embedded in a soft shell such as foam within the pillow or another pliable object, coupled to an interior surface of the pillow or another pliable object, coupled to an interior surface of the vest, etc.), positioned in an exterior surface of the body (e.g., woven into a casing of the pillow or another pliable object, woven into the outer material of the vest, etc.), coupled to the exterior surface of the body (e.g., coupled to an exterior surface of the pillow or another pliable object, coupled to an exterior surface of the vest), etc. For instance, the stethoscope heads 104a, 104b, 104c, 104d, and EKG leads 106a, 106b, 106c of FIG. 1 may be embedded within the pillow's soft shell, a pulse oximeter may be positioned on an exterior surface of the pillow, a temperature probe may be positioned on an exterior surface of the pillow, etc.

Further, the sensing devices disclosed herein may be in direct and/or indirect contact with the skin of a user when sensing one or more physiological parameters of the user. For example, some of the sensing devices may effectively sense one or more physiological parameters of a user without being in contact with the user's skin. In such examples, the sensing devices may sense the one or more physiological parameters through another object such as a piece of clothing (e.g., a shirt, etc.). Example sensing devices that may not require skin contact (e.g., contactless sensors) may include, for example, stethoscope heads/sensors, BCG sensors, etc. In other examples, some of the sensing devices disclosed herein may require skin contact to effectively sense one or more physiological parameters of the user. Example sensing devices requiring skin contact may include, for example, temperature sensors/probes, PPG sensors, etc. Further, some sensing devices such as EKG leads (e.g., electrodes) may effectively sense one or more physiological parameters through direct and/or indirect contact with the user's skin depending on, for example, which type of EKG leads are employed.

The sensing devices disclosed herein may be strategically positioned to capture particular data of the user. For example, the stethoscope heads 104a, 104b, 104c, 104d of FIG. 1 may be positioned to capture data (e.g., sound) corresponding to upper and lower portions of each lung of the user. For instance, the stethoscope heads 104a, 104d may capture data correspond to an upper portion and a lower portion, respectively, of one of the lungs. Additionally, the EKG leads 106a, 106b, 106c of FIG. 1 may correspond to an augmented vector right (aVR) lead, an augmented vector left (aVL) lead, and/or an augmented vector foot (aVF) lead. When a user is in contact with the body, the aVR lead may be positioned adjacent to the right upper extremity of the user's body, the aVL lead may be positioned adjacent to the left upper extremity of the user's body, and the aVF lead may be positioned adjacent to the left lower extremity of the user's body. In other examples, any one of the stethoscope heads 104a, 104b, 104c, 104d and/or EKG leads 106a, 106b, 106c may be positioned in another suitable location if desired. For example, the EKG leads 106a, 106b, 106c and three other EKG leads may represent precordial leads V1 through V6 and may be positioned accordingly on the pliable object.

As explained herein, the sensing devices are in communication a control circuit. For example, the sensing devices may be in communication with the control circuit via a wireless and/or wired connection. As such, the control circuit may receive data from the detachable sensing devices and/or the physically attached sensing devices (e.g., the devices embedded within the body, positioned in and/or on a surface of the body, etc.) via a wireless connection (e.g., a Bluetooth, an RF module, etc.) and/or a wired connection. In some examples, one or more of the sensing devices (e.g., a digital scale) may provide data to the control circuit via a wireless connection, and without physically attaching to and/or detachably coupling to the body.

The control circuit disclosed herein may include an analog control circuit, a digital control circuit (e.g., a digital signal controller (DSC), a digital signal processor (DSP), a microprocessor, a microcontroller, etc.), or a hybrid control circuit (e.g., a digital control unit and an analog circuit). In some examples, any one of the control circuits may be a component on a circuit board (e.g., a printed circuit board) such as a motherboard. In such examples, the circuit board may include the control circuit, filter(s), input connectors, receiver/transceiver modules, etc.

Additionally, the control circuits may be positioned in any suitable location. For example, any one of the control circuits may be embedded within its associated body. In other examples, any one of the control circuits may be positioned external to its associated body. In such examples, a transmitter may be embedded within the body, and in communication with the external control circuit.

In some examples, any one of the control circuits may be in communication with a computing device such as a server (e.g., a cloud-based server, etc.) a smart phone, a tablet, a laptop, etc. In such examples, the computing device may receive data relating to one or more vital signs of the user. Such data may include sensed data from the sensing device and collected by the control circuit, derived (e.g., processed) data based on the sensed data, etc.

For example, FIG. 9 illustrates a system 900 including a body 902 and a computing device 904. As shown, the body 902 includes two sensing devices 906a, 906b, and a control circuit 908 in communication with the sensing devices 906a, 906b. For example, the control circuit 908 and the sensing devices 906a, 906b may be in communication with each other via a wireless and/or a wired connection as explained above. As such, the control circuit 908 may receive, from the sensing devices 906a, 906b, physiological parameters of a user.

The sensing devices 906a, 906b may include any suitable devices for sensing vital signs and/or other desirable data of a user as explained above. For example, each sensing device 906a, 906b may include any one of the devices disclosed herein such as a stethoscope head (and a corresponding microphone), an EKG lead, a temperature probe/sensor, a pulse oximeter, a PPG sensor, a BCG sensor, etc.

In the example of FIG. 9, the body 902 may be any one of the bodies disclosed herein or another suitable device. For example, the body 902 may be a pillow, a pad, a vest, a backpack, etc.

As shown in FIG. 9, the computing device 904 is in communication with the control circuit 908. This allows the computing device 904 to receive physiological parameters sensed by the sensing devices 906a, 906b and/or data derived from the sensed physiological parameters. For example, the computing device 904 may include a software application 910 that generates a warning based on the physiological parameters, displays the physiological parameters (and/or characteristics derived from the physiological parameters) on a display 912, and/or transmits the warning and/or the physiological parameters to a healthcare worker such as a doctor, nurse, etc. In some examples, the computing device 904 may provide data, commands, etc. to the control circuit 908. The computing device 904 and the control circuit 908 may send and/or receive data via a wireless connection such as a local wireless network such as Bluetooth, Wi-Fi, etc. and/or a wired connection.

Physiological parameters from the sensing devices 906a, 906b may be processed by the control circuit 908 and/or the computing device 904 (e.g., a control circuit such as a processor 914 in the computing device 904). In some examples, the system 900 may include one or more filters (not shown) for reducing noise in signals (e.g., analog signals) from the sensing devices 906a, 906b. The filters may be components of the control circuit 908 and/or external to the control circuit 908.

Each of the bodies disclosed herein may be positioned on a chair, a bed, a floor, a wall, and/or another suitable location to allow a user to recline against and contact the body. The chair, the bed, etc. may be located in a hospital, a doctor's office, a user's home, etc. This may allow the user to position his/her back, chest, etc. against the body as desired. In some embodiments, the user may hold the body against his/her chest without placing the body on a chair, a bed, etc.

Figures 10, 11, 12, 13:
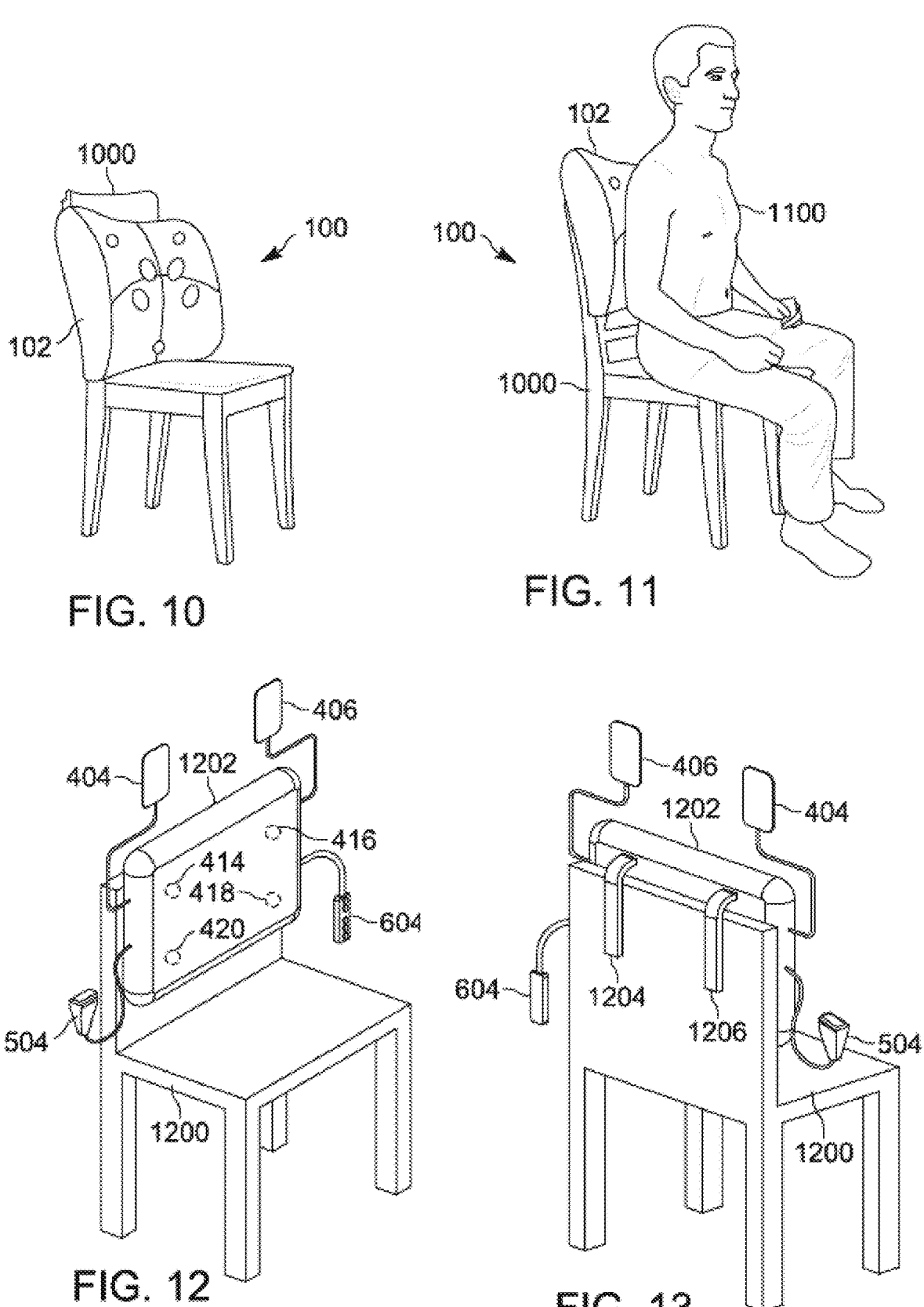
FIG. 10 is perspective view of the pillow of FIG. 1 positioned on a chair according to this embodiment of the present disclosure.
FIG. 11 is a perspective view of the pillow of FIG. 1 positioned on a chair and a user resting against the pliable object according to this embodiment of the present disclosure.
FIG. 12 is a front isometric view of a chair and a pliable object positioned on the chair according to another example embodiment.
FIG. 13 is a rear isometric view of the chair and the pliable object of FIG. 12.

For example, FIGS. 10 and 11 illustrate a chair 1000 and the system 100 of FIG. 100 including the body 102 positioned on the chair 1000. Specifically, the body 102 is placed on a backrest portion of the chair 1000. This allows a user 1100 to sit in an upright position on the chair 1000 and rest his/her back against (and contact) the body 102, as shown in FIG. 11. In other examples, the user 1100 may sit on the chair 1000 in another manner such that the user's chest rests against (and contacts) the body 102. In such examples, legs of the user 1100 may extend on opposing sides of the backrest of the chair 1000.

In some examples, the bodies disclosed herein may be adjustable to accommodate different users. For example, the body 102 of FIG. 1 may include one or more fasteners such as brackets, straps, etc. to allow a user to adjust the position of the body 102 relative to a chair, a bed, etc. This may allow users having of different heights, body types, etc. to contact the body (e.g., the body 102, etc.) as desired. For instance, the brackets, straps, etc. may be adjusted to move the body 102 (e.g., vertically and/or horizontal) along the backrest portion of the chair 1000 of FIGS. 10 and 11 to accommodate different users. For example, the body 102 may be positioned near a lower end of the backrest portion of the chair 1000 as shown in FIG. 10, near an upper end of the backrest portion of the chair 1000 as shown in FIG. 11, etc.

FIGS. 12 and 13 illustrate another example of a chair 1200 and a body 1202 (e.g., a pliable object) positioned on a backrest of the chair 1200. In the example of FIGS. 12 and 13, the body 1202 includes the defibrillator paddles 404, 406 of FIG. 4, the sensing devices 414, 416, 418, 420 of FIG. 4, the ultrasound probe 504 of FIG. 5, the user control device 604 of FIG. 6, and a control circuit (not shown) in communication with the defibrillator paddles 404, 406, the sensing devices 414, 416, 418, 420, and the user control device 604.

In the example of FIGS. 12 and 13, a user may sit in the chair 1200 to utilize the various components of the body 1202. For example, the user may sit in the chair 1200 in a forward manner so that the user's back rests against (and contacts) the body. Alternatively, the user may sit in the chair 1200 in a backward manner so that the user's chest rests against (and contacts) the body 1202

In some embodiments, the body 1202 may further include optional straps 1204, 1206 extending from a top portion of the body 1202 as shown in FIG. 13. The straps 1204, 1206 may extend about a portion of the backrest of the chair 1200 to secure the body 1202 to the chair 1200. In some examples, the straps 1204, 1206 may be adjustable to alter the position of the body 1202 relative to the chair 1200. For example, the straps 1204, 1206 may be adjusted to move the body 1202 along the backrest of the chair 1200 as desired.

FIGS. 14 and 15 illustrate other example configurations of a user sitting in a chair and employing a body as disclosed herein. Specifically, in FIG. 14, a user 1404 is sitting in an upright position in a chair 1400 while holding a body 1402 against his/her chest. In FIG. 15, the user 1404 is sitting in a reclined position in a chair 1500 while holding the body 1402 against his/her chest. In such examples, the body 1402 may be any suitable body disclosed herein including, for example, any one of the bodies 102, 202, 302, 402, 502, 602, 702, 1202, etc.

The systems disclosed herein may be configurable to capture various vital signs of a user. For example, sensing devices of any one of the systems may capture data relating to lung sounds, heart sounds, respiratory rates, heart rates, heart rhythms, etc. In some examples, the EKG sensing devices may capture standard variables. Additionally, any one of the control circuits disclosed herein may include instructions (e.g., instructions stored in memory of the control circuit) to analyze respiratory rates, inspiratory to expiratory ratios (I:E ratios), heart rates, heart rhythms, etc. The control circuits may also analyze lung sounds to determine if the sounds are normal and/or abnormal, if the sounds include wheezes and/or crackles, etc. Further, the control circuits may also analyze heart sounds, heart rates, heart rhythms, etc. to determine if heart murmurs, cardiac arrhythmias, etc. are present. The data (including the analyzed data) may be provided to healthcare workers, saved for future use, etc.

Figure 17:
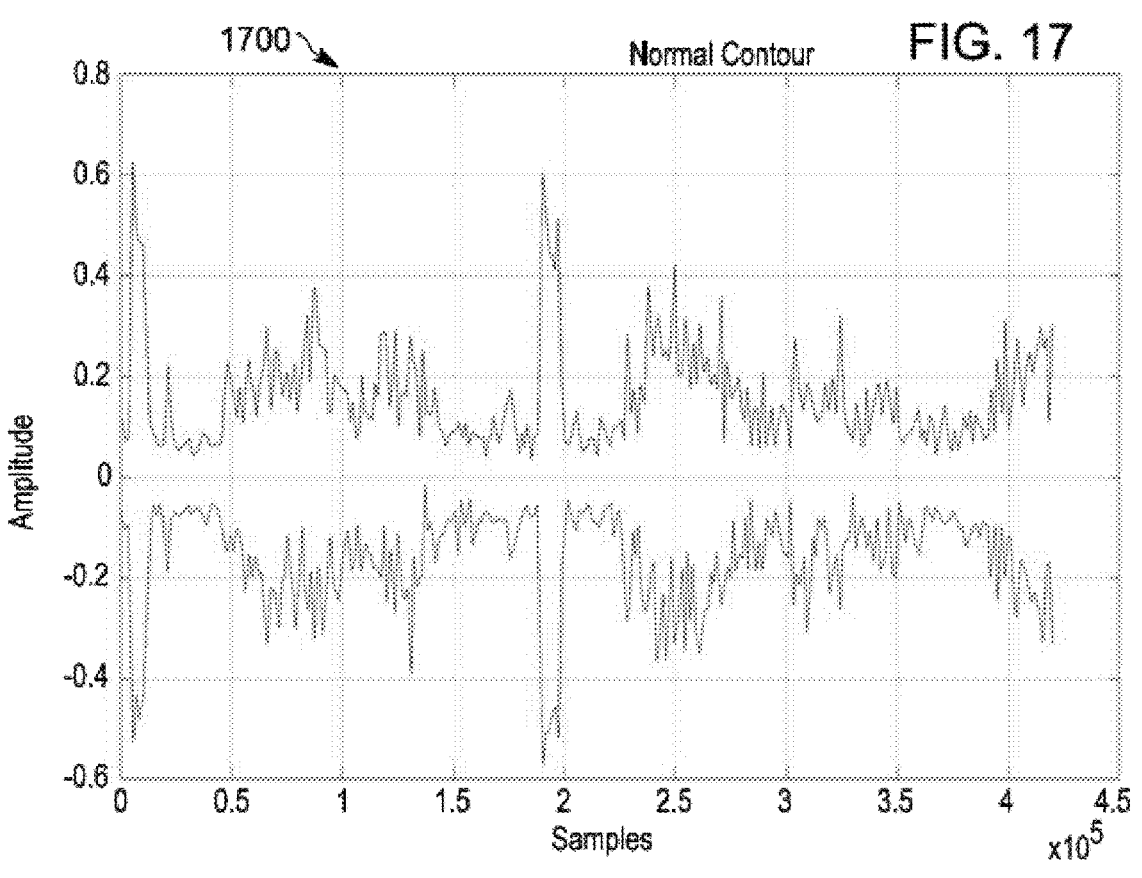
FIG. 17 is a graph of contour lines for the signal of FIG. 16.
Figure 18:
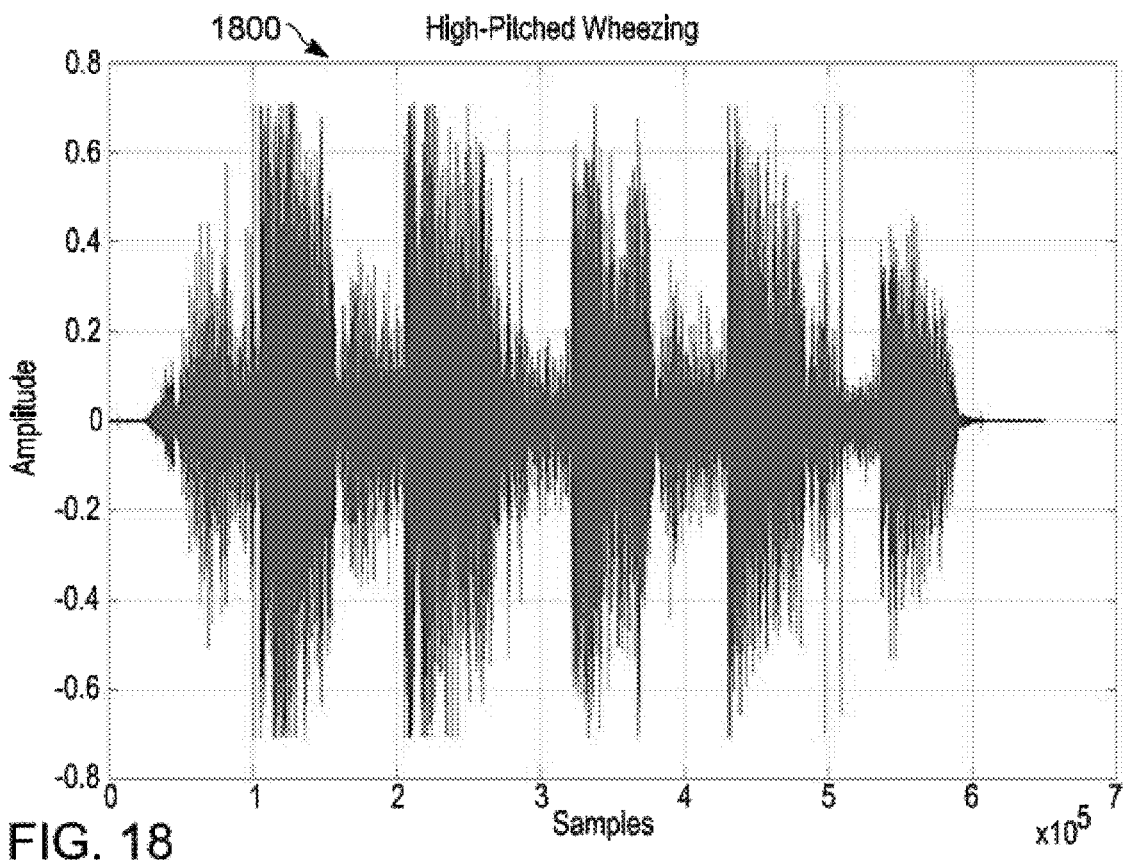
FIG. 18 is a graph of a signal representing wheezing lung sounds from a user using one embodiment of the present disclosure.
Figures 19, 20:
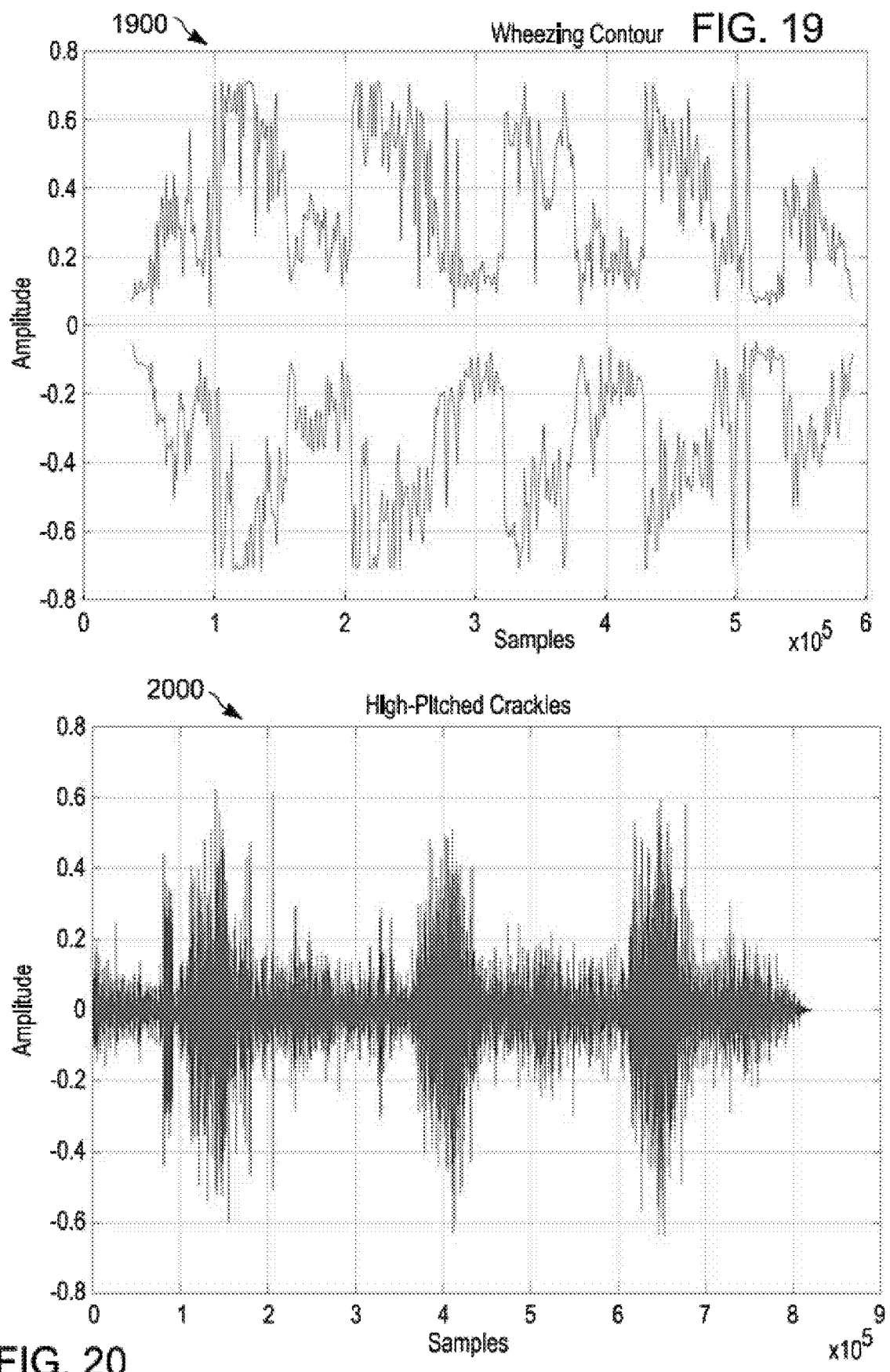
FIG. 19 is a graph of contour lines for the signal of FIG. 18.
FIG. 20 is a graph of a signal representing crackle lung sounds from a user using one embodiment of the present disclosure.
Figure 21:
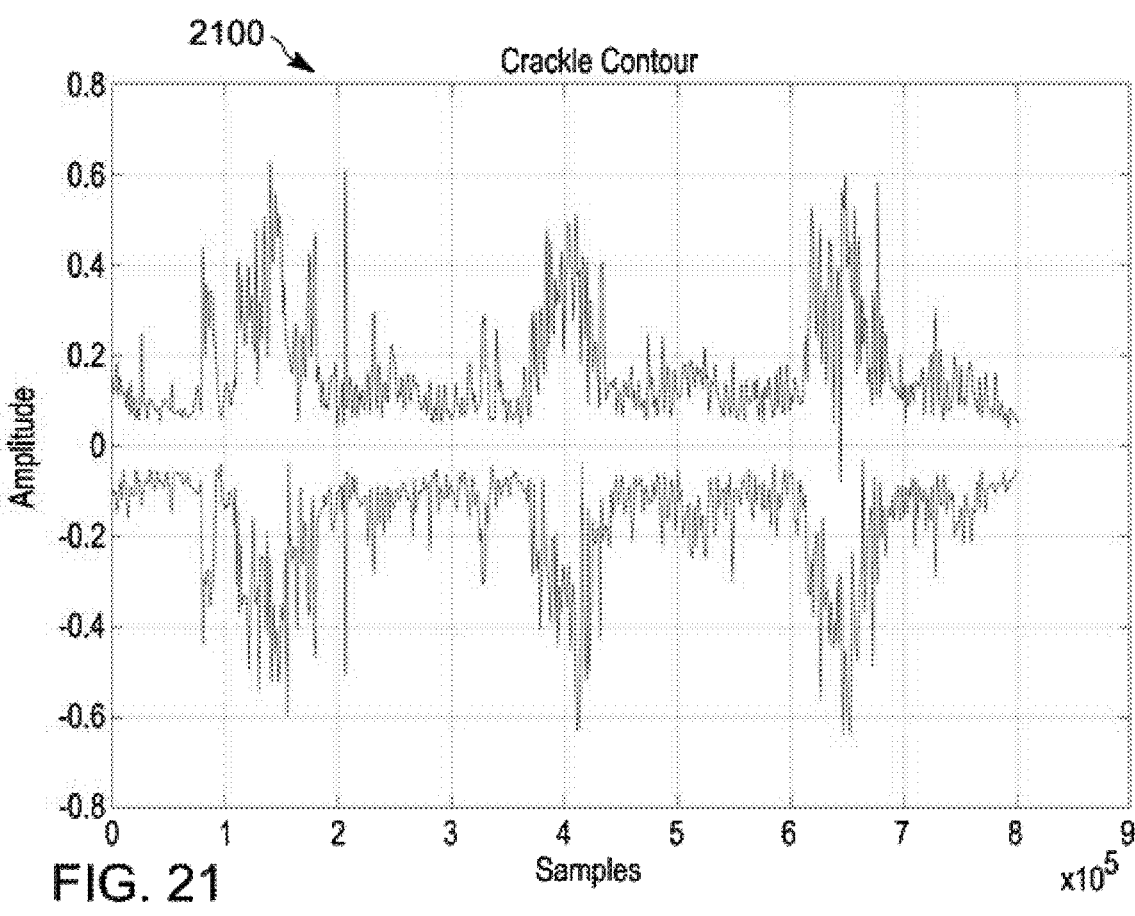
FIG. 21 is a graph of contour lines for the signal of FIG. 20.

For example, FIGS. 16, 18 and 20 illustrate graphs 1600, 1800, 2000 of example signals representing lung sounds (e.g., breath sounds) of a user sensed by any one of the stethoscope sensing devices disclosed herein, and FIGS. 17, 19 and 21 illustrate graphs 1700, 1900, 2100 of example contour lines of the signals shown in FIGS. 16, 18 and 20. The graphs 1600, 1700, 1800, 1900, 2000, and 2100 show how normal, wheezing, and crackle lung sounds look different (just as they sound different). Specifically, the graph 1600 of FIG. 16 represents normal vesicular breath sounds, the graph 1800 of FIG. 18 represents high-pitched wheezing sounds, and the graph 2000 of FIG. 20 represents high-pitched crackling sounds. The graph 1700 of FIG. 17 represents contour lines for the normal breath sounds shown in FIG. 16, the graph 1900 of FIG. 19 represents contour lines for the wheezing sounds shown in FIG. 18, and the graph 2100 of FIG. 21 represents contour lines for the crackling sounds shown in FIG. 20. As explained above, any one of the control circuits disclosed herein may analyze lung sounds detected by the stethoscope sensing device(s), and extract contour lines of the lung sounds for diagnostic purposes.

In some examples, a baseline may be created based on previous breath sounds of a user. This baseline data may be compared to current breath sounds of the user to detect changes in the user's breath sounds over time. For example, the normal breath sounds of the graphs 1600, 1700 may represent baseline breath sounds of a user. The wheezing sounds and/or the crackling sounds of the graphs 1800, 1900, 2000, and 2100 may represent the user's breath sounds later in time. The control circuit may compare data (e.g., amplitude values, frequency of increased amplitude values, duration of increased amplitude values, etc.) from the normal breath sounds and the wheezing and/or the crackling sounds, and generate a warning (e.g., an alert) for a doctor, a nurse, a user, etc. In other examples, the control circuit may provide graphical data to the doctor, the nurse, the user, etc.

Figure 22:
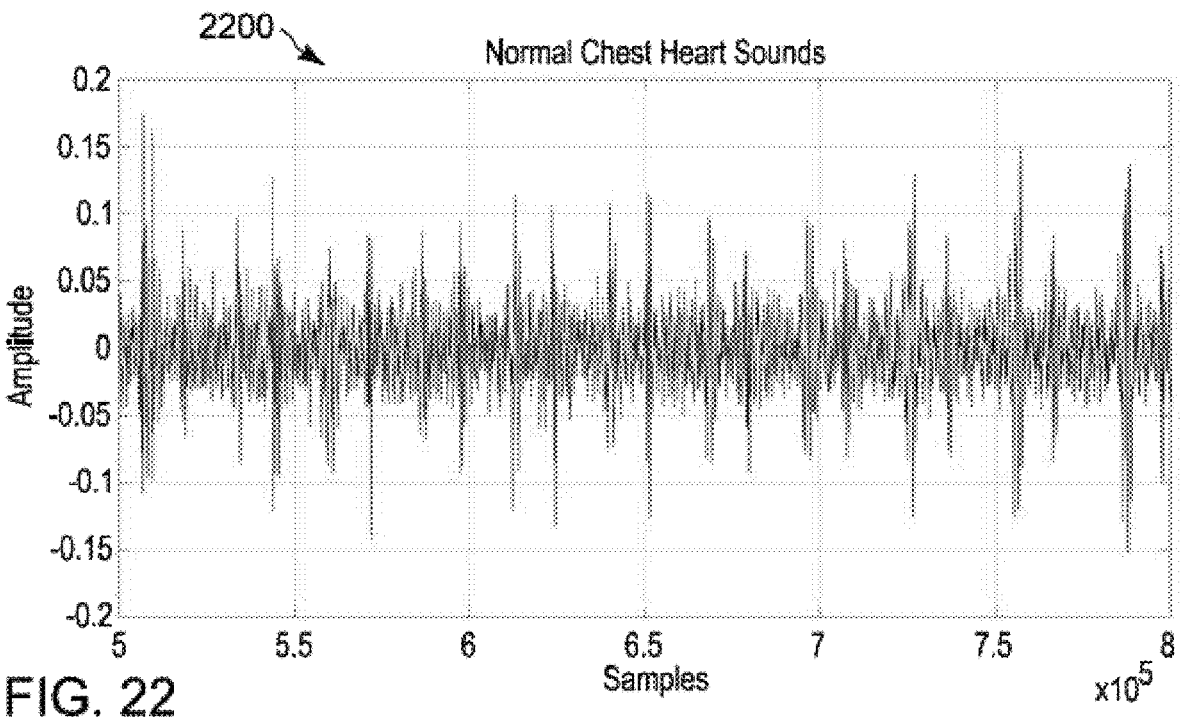
FIG. 22 is a graph of a signal representing heart sounds from a user using one example embodiment of the present disclosure.
Figure 23:
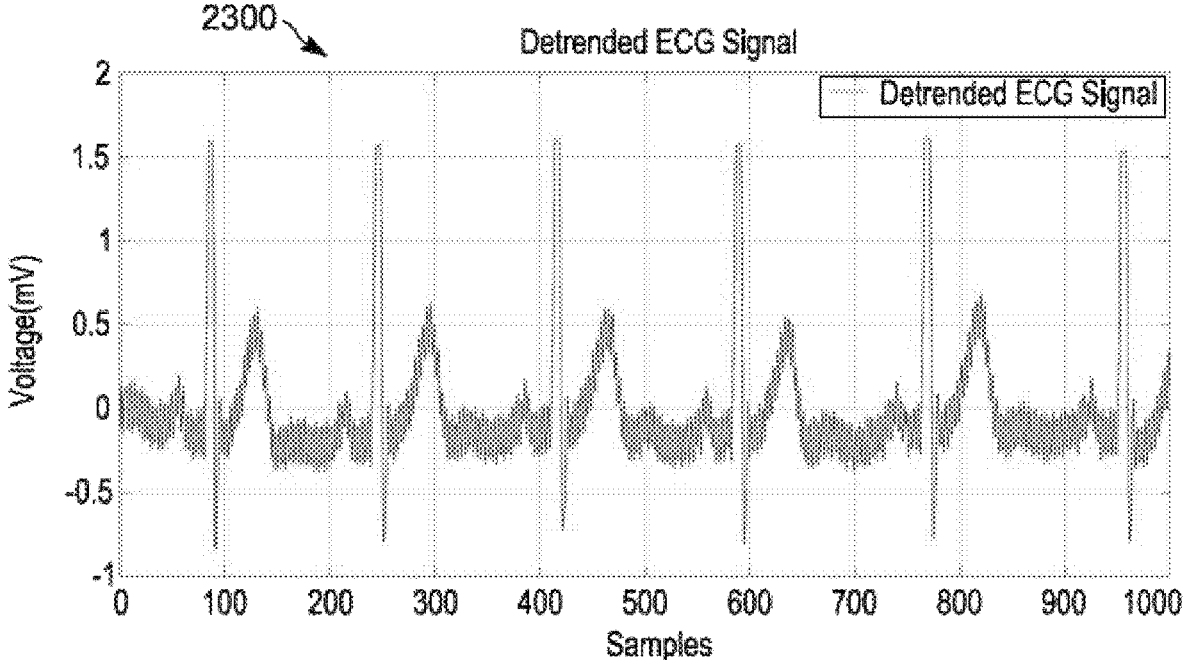
FIG. 23 is a graph of a detrended electrocardiogram (ECG) signal according to a user using one example embodiment of the present disclosure.
Figure 24:
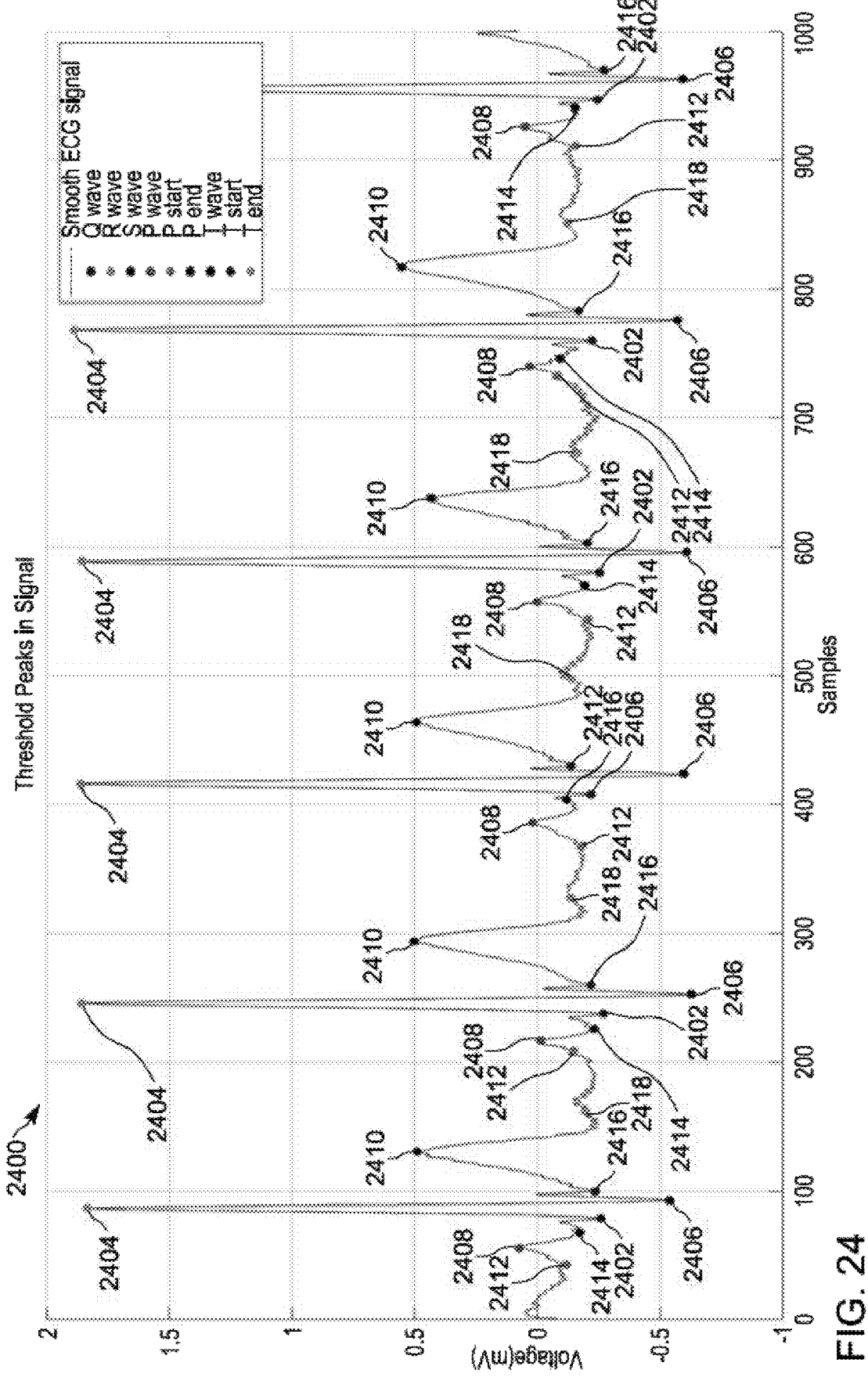
FIG. 24 is a graph of threshold peaks in the ECG signal of FIG. 23.

FIGS. 22-24 illustrate graphs 2200, 2300, 2400 of example signals representing heart sounds of a user sensed by any one of the stethoscopes and EKG (e.g., ECG) sensing devices disclosed herein. Specifically, the graph 2200 of FIG. 22 represents normal heart sounds from the stethoscope, the graph 2300 of FIG. 23 represents a detrended ECG signal, and the graph 2400 of FIG. 24 shows peaks in the ECG signal of FIG. 23. For example, the graph 2400 shows peaks for various waves (e.g., Q, R, S, P, T waves). Specifically, points 2402, 2404, 2406, 2408, 2410 represent peaks of Q, R, S, P, T waves, respectively, over multiple cycles. Additionally, points 2412, 2414 represent a start and an end of the P wave, respectively, and points 2416, 2418 represent a start and an end of the T wave, respectively, over multiple cycles.

Any one of the control circuits disclosed herein may analyze heart sounds detected by the stethoscopes, extract a detrended ECG signal, and detect key ECG features (e.g., features relating to the Q, R, S, P, T waves) as shown in the graph 2400 of FIG. 24 for diagnostic purposes. In some examples, the control circuit(s) may provide data to a healthcare worker, a user (e.g., patient), etc. based on the graph 2400. Such data may include, for example, a beat rate data (e.g., 0.812645 seconds per beat, 48.758715 beats per minutes, etc.), an average rise time (e.g., 39 msec), an average fall time (e.g., 34 msec), an average rise level (e.g., 10 msec), an average fall level (e.g., 12 msec), an average QRS complex (e.g., 73 msec), an average PR segment (e.g., 41 msec), an average PR interval (e.g., 164 msec), an average ST segment (e.g., 31 msec), an average QT interval (e.g., 425 msec), etc. Additionally, and similar to the lung sounds explained above, a baseline may be created based on previous heart sounds of a user. This baseline data may be compared to current heart sounds of the user to detect changes over time.

In various embodiments, the systems disclosed herein may be configurable to obtain a blood pressure of a user, with or without employing a sphygmomanometer such as the sphygmomanometer 314 of FIG. 3. For example, a blood pressure of a user may be estimated based on signals from one or both of a PPG sensor (e.g., the PPG sensor 208 of FIG. 2, etc.) and a BCG sensor (e.g., the BCG sensor 210 of FIG. 2, etc.), in conjunction with signals from one or more EKG leads (e.g., one or more of the EKG leads 206a, 206b, 206c, 206d of FIG. 2, etc.).

FIGS. 25-28 illustrate graphs of example PPG, ECG, and/or BCG waveforms that may be used to estimate a blood pressure of a user. Any one of the control circuits disclosed herein may analyze one or more waveforms of FIGS. 25-28, and estimate a user's blood pressure based on the waveform(s).

Figure 25:
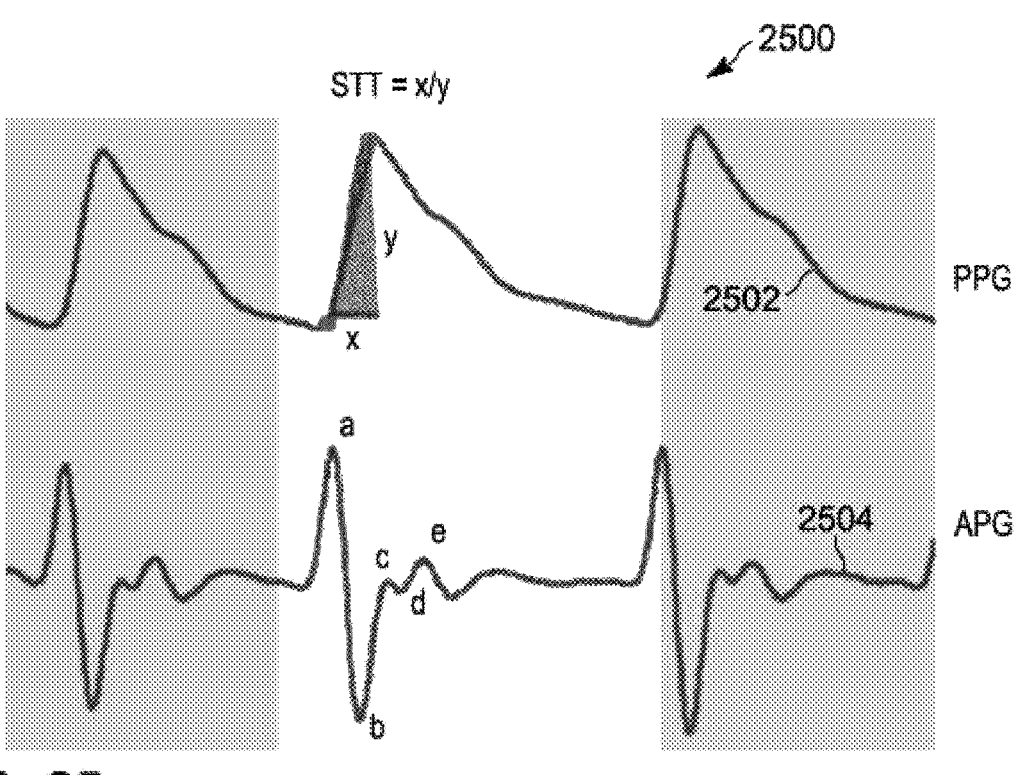
FIG. 25 is a graph of PPG and accelerated photoplethysmograph (APG) waveforms usable to estimate a user's blood pressure according to another example embodiment of the present disclosure.

For example, FIG. 25 illustrates a graph 2500 of a PPG waveform 2502 and an accelerated photoplethysmograph (APG) waveform 2504. An APG signal (e.g., the waveform 2504) is a second-order differential of a PPG signal (e.g., the waveform 2502). As shown, a slope transit time (STT) is determined between a foot and a peak of the PPG waveform 2502. Specifically, a STT value is determined by dividing the rise (y) by the run (x) between the foot and the peak of the PPG waveform 2502. In some examples, a systolic blood pressure may be estimated based on the STT value of the PPG waveform 2502.

Additionally, the APG waveform 2504 may be employed to estimate a blood pressure of a user. For instance, and as shown in FIG. 25, peaks a, b, c, d, e corresponding to different waves may be determined in the APG waveform 2504. For example, the waves corresponding to peaks a, b are systolic anterior components (e.g., driving pressure waves caused by blood ejection), the waves corresponding to peaks c, d are systolic posterior components (e.g., reflection pressure waves where the driving pressure waves propagated to the periphery and then came back), and the wave corresponding to peak e is a diastolic component (e.g., a peripheral blood flow after an aortic valve closes). A blood pressure of a user may be estimated based on the waves corresponding to peaks a, b, c, d, e. For example, an increase in a systolic blood pressure generally causes the peak a to increase and the peaks b, e to decrease, and an increase in a diastolic blood pressure generally causes the peak a to decrease and the peaks b, e to increase.

Figure 26:
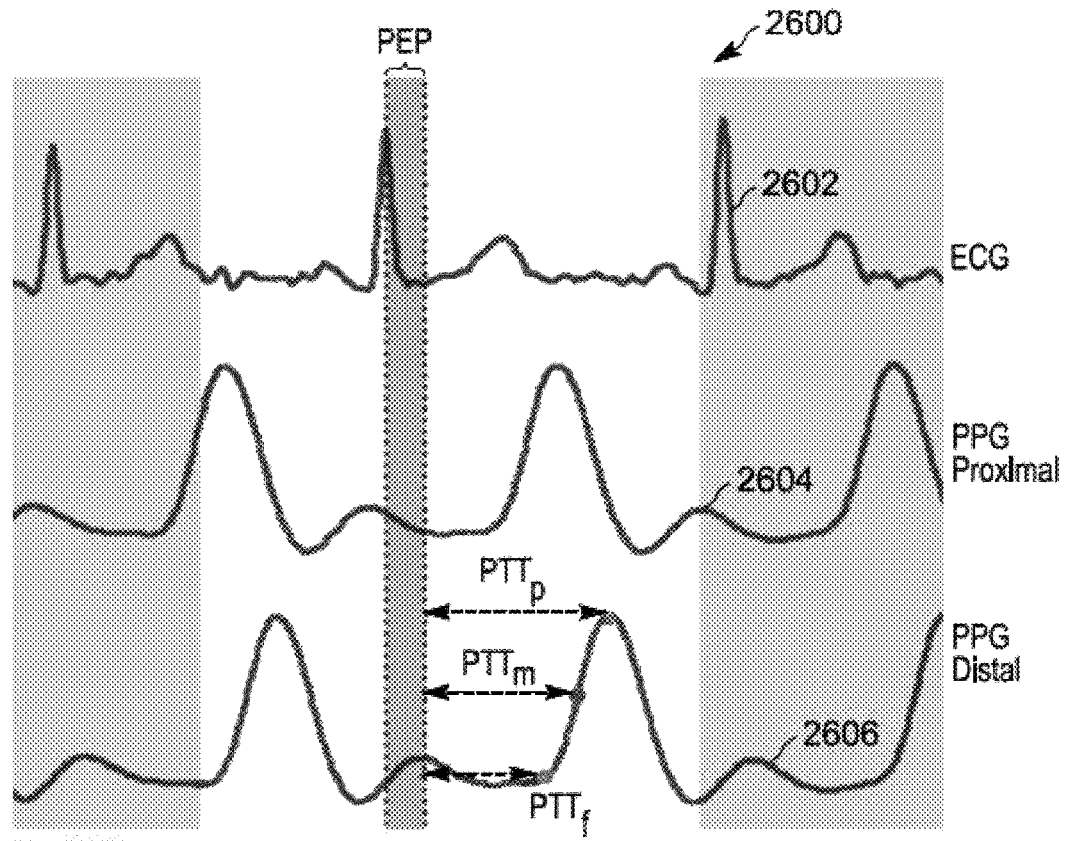
FIG. 26 is a graph of ECG and PPG waveforms usable to estimate a user's blood pressure according to another example embodiment of the present disclosure.

FIG. 26 illustrates a graph 2600 of an ECG waveform 2602 and PPG waveforms 2604, 2606. The PPG waveforms 2604, 2606 represent signals from PPG sensors located at different sites (e.g., proximal and distal sites) of a user. As shown in FIG. 26, a pulse arrival time (PAT) may be determined based on the sum of a pre-ejection time (PEP) and a pulse transit times (PTT). PEP may be a time period between the opening of an aortic valve (e.g., an R-peak of an ECG signal) and a q-wave of an ECG signal, and PTT may be a time period for a pulse to propagate from a proximal site to a distal site.

In some examples, a blood pressure may be estimated based on PAT. For example, a blood pressure may be estimated based on different values of PAT, which are calculated based on different PTT values. For instance, PAT may be calculated based on a time interval from a peak of the ECG waveform 2602 to a foot of the PPG waveform 2606 (e.g., PATf=PEP+PTTf), a time interval from a peak of the ECG waveform 2602 to a maximum slope point of the PPG waveform 2606 (e.g., PATm=PEP+PTT$_m$), and/or a time interval from a peak of the ECG waveform 2602 to a peak of the PPG waveform 2606 (e.g., PAT$_P$=PEP+PTTp).

Figures 27, 28:
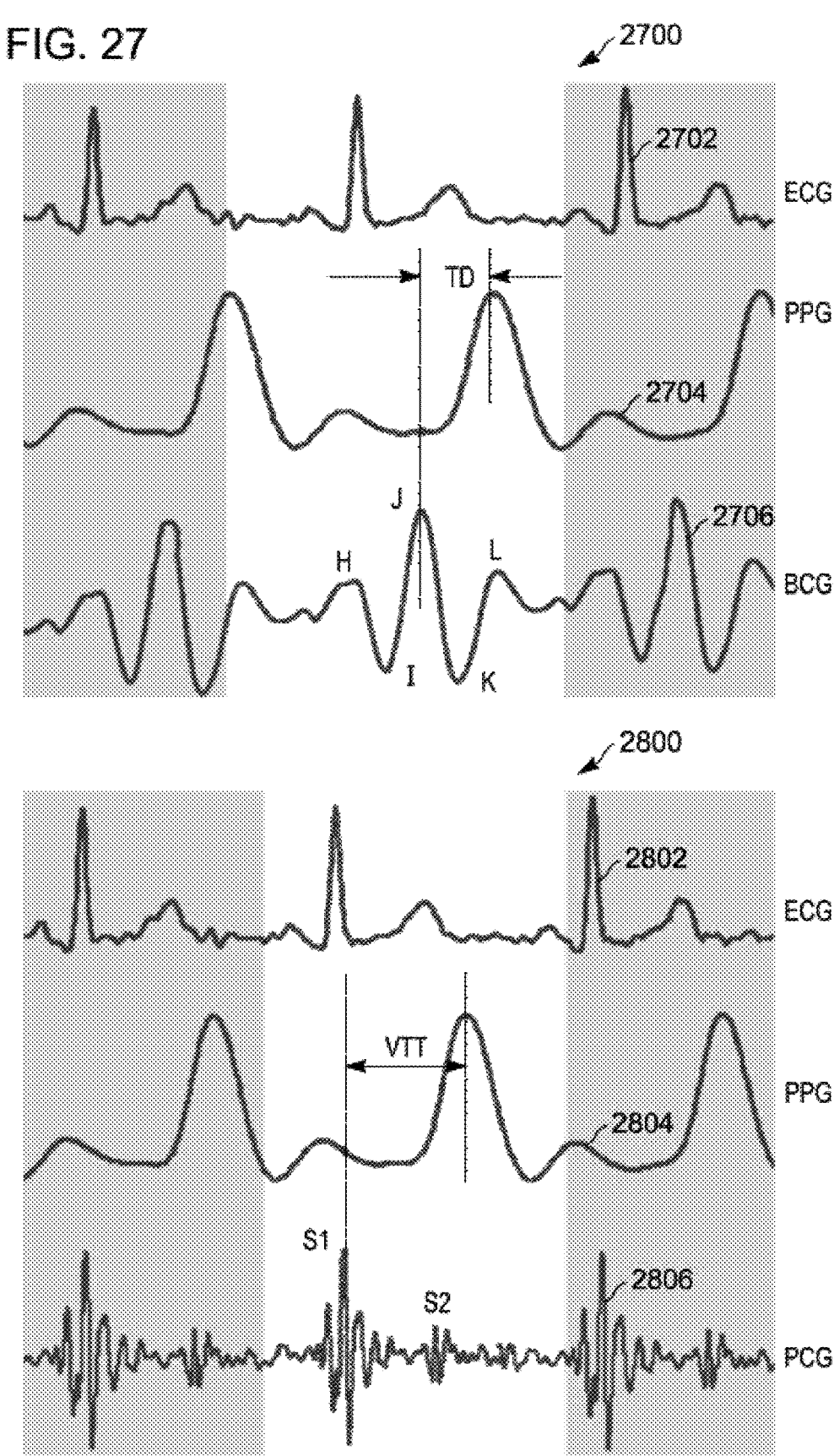
FIG. 27 is a graph of ECG, PPG, and BCG waveforms usable to estimate a user's blood pressure according to another example embodiment of the present disclosure.
FIG. 28 is a graph of ECG, PPG, and (phonocardiograph) PCG waveforms usable to estimate a user's blood pressure according to another example embodiment of the present disclosure.

[00118] FIG. 27 illustrates a graph 2700 of an ECG waveform 2702, a PPG waveform 2704, and a BCG waveform 2706. In various embodiments, a blood pressure may be estimated based on the PPG waveform 2704 and the BCG waveform 2706. For example, and as shown in FIG. 27, peaks H, I, J, K, L corresponding to different waves may be determined in the BCG waveform 2706, and a time difference TD may be determined based on the PPG waveform 2704 and the BCG waveform 2706. For instance, TD may represent an interval between the J peak in the BCG waveform 2706 and a systolic peak in the PPG waveform 2704, as shown in FIG. 27. In some cases, a blood pressure may be estimated based on the TD interval.

FIG. 28 illustrates a graph 2800 of an ECG waveform 2802, a PPG waveform 2804, and a phonocardiograph (PCG) waveform 2806. In some examples, one or more stethoscopes (and associated microphones) may be employed to obtain the PCG waveform 2806. In various embodiments, a blood pressure may be estimated based on the PPG waveform 2804 and the PCG waveform 2806. For example, and as shown in FIG. 28, two heart sounds (of a heat beat) are designated by S1 and S2 on the PCG waveform 2806, and a vascular transit time (VTT) is determined based on the PPG waveform 2804 and the PCG waveform 2806. For instance, VTT may represent an interval from the first heart sound S1 of the PCG waveform 2806 and a systolic peak of the PPG waveform 2804, as shown in FIG. 28. In some cases, a blood pressure may be estimated based on the VTT interval. In some examples, data from sensing device(s) for various patients (e.g., users) may be viewable on a graphical user interface (GUI) of any one of the computing device disclosed herein. For example, the computing device's GUI may provide various inputs to allow a healthcare worker, a user, etc. to select and view data relating to a patient's lung sounds, heart sounds, temperature, oximeter readings, blood pressure, etc. Additionally, the healthcare worker, the user, etc. may select one or more inputs on the GUI to instruct the sensing device(s) to sense new data relating to the patient's lung sounds, heart sounds, temperature, oximeter readings, blood pressure, etc.

Employing the teachings herein, detections of deterioration, predictions of deterioration, etc. of users may be identified. For example, one or more signals from the sensing devices disclosed herein may be utilized to detect early signs of clinical deterioration and/or predict future deterioration of chronic obstructive lung disease (COPD), congestive heart failure (CHF), asthma, acute myocardial infarctions, etc.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Whereas particular embodiments of this invention have been described above for purposes of illustration, it will be evident to those skilled in the art that numerous variations of the details of the present invention may be made without departing from the scope of the invention as defined in the appended claims.

What is claimed is:

1. A method of monitoring physiological parameters of a user, the method comprising the steps of:

Providing a system for monitoring physiological parameters of a user having a pliable body, with a plurality of physiologic sensing devices mounted within the pliable body, the plurality of physiologic sensing devices including i) sensors detecting at least lung sounds and heart sounds from the user including a plurality of stethoscopes each having a stethoscope head configured for obtaining at least lung sounds and heart sounds of the user wherein at least one stethoscope is above a horizontal midline of the pliable body, wherein at least one stethoscope is below the horizontal midline of the pliable body, wherein at least one stethoscope is left of a vertical midline of the pliable body, and wherein at least one stethoscope is left of a vertical midline of the pliable body, and ii) sensors detecting EKG signals from the user including at least three electrocardiogram leads, and a wireless communication device for transmitting at least lung sounds, heart sounds and EKG signals detected from the subject;

Removably positioning the system for monitoring physiological parameters of the user on the backrest of a chair;

Positioning the system for monitoring physiological parameters of the user against the back of the user by having the user sit in the chair;

Sensing at least lung sounds, heart sounds and EKG signals from the user from the posterior chest of the user via the system for monitoring physiological parameters of the user;

Transmitting at least lung sounds, heart sounds and EKG signals detected through the posterior chest of the user to a computer to monitor physiological parameters of the user.

2. The method of monitoring physiological parameters of a user according to claim 1, wherein the lung sounds detected are utilized to define detected respiratory variables including respiratory rates of the user.

3. The method of monitoring physiological parameters of a user according to claim 1, wherein the lung sounds detected are utilized to define detected respiratory variables including Inspiratory to expiratory ratios of the user.

4. The method of monitoring physiological parameters of a user according to claim 1, wherein the lung sounds detected are utilized for detecting and identifying sounds that are abnormal including wheezes and crackles.

5. The method of monitoring physiological parameters of a user according to claim 1, wherein the heart sounds detected are utilized to define detected heart variables including heart rates of the user.

6. The method of monitoring physiological parameters of a user according to claim 1, wherein the heart sounds detected are utilized to define detected heart variables including heart rhythms of the user.

7. The method of monitoring physiological parameters of a user according to claim 1, wherein the heart sounds detected are utilized to define and identify any cardiac arrhythmias of the user.

8. The method of monitoring physiological parameters of a user according to claim 1, wherein the heart sounds detected are utilized to define and identify any cardiac murmurs of the user.

9. The method of monitoring physiological parameters of a user according to claim 1, wherein the plurality of physiologic sensing devices mounted within the pliable body includes at least one PPG sensor.

10. The method of monitoring physiological parameters of a user according to claim 1, wherein the system for monitoring physiological parameters of a user incudes at least one PPG sensor external to the pliable body.

11. The method of monitoring physiological parameters of a user according to claim 1, wherein the plurality of physiologic sensing devices mounted within the pliable body includes at least one of a temperature sensor, a ballistocardiograph sensor, or an ultrasound probe.

12. The method of monitoring physiological parameters of a user according to claim 1, wherein the EKG signals are used to detect acute myocardial infarction.

13. The method of monitoring physiological parameters of a user according to claim 1, wherein the plurality of physiologic sensing devices mounted within the pliable body are configured to detect early signs of clinical deterioration or predict future deterioration of at least one of chronic obstructive lung disease (COPD), congestive heart failure (CHF), asthma, and acute myocardial infarctions.

14. The method of monitoring physiological parameters of a user according to claim 1, wherein the system is configured to communicate select messages from the user to a medical professional.

15. The method of monitoring physiological parameters of a user according to claim 1, wherein the system is configured to be adjustably positioned on the back of the chair to accommodate different users.

16. The method of monitoring physiological parameters of a user according to claim 1, wherein the system includes straps for positioning the system on the back of the chair.

17. The method of monitoring physiological parameters of a user according to claim 1, wherein the computer is configured to graphically display the monitored physiological parameters of the user.

18. A system for monitoring physiological parameters of a user, the system comprising:

a pliable body configured to be removably positioned on the backrest of a chair;

a plurality of physiologic sensing devices mounted within the pliable body, the plurality of physiologic sensing devices including i) sensors configured for detecting at least lung sounds and heart sounds from a posterior chest wall of a user including i) a plurality of stethoscopes each having a stethoscope head configured for obtaining at least lung sounds and heart sounds of the user wherein at least one stethoscope is above a horizontal midline of the pliable body, wherein at least one stethoscope is below the horizontal midline of the pliable body, wherein at least one stethoscope is left of a vertical midline of the pliable body, and wherein at least one stethoscope is left of a vertical midline of the pliable body, and ii) sensors detecting EKG signals from the posterior chest wall of the user including at least three electrocardiogram leads;

a wireless communication device for transmitting at least lung sounds, heart sounds and EKG signals detected from the posterior chest wall of the user;

a computer configured to receive and display at least the transmitted lung sounds, heart sounds and EKG signals detected through the posterior chest of the user to monitor physiological parameters of the user.

* * * * *